(12) United States Patent
Takahashi et al.

(10) Patent No.: US 7,755,753 B2
(45) Date of Patent: Jul. 13, 2010

(54) DEFECT INSPECTION APPARATUS, SENSITIVITY CALIBRATION METHOD FOR THE SAME, SUBSTRATE FOR DEFECT DETECTION SENSITIVITY CALIBRATION, AND MANUFACTURING METHOD THEREOF

(75) Inventors: Naohiro Takahashi, Kawasaki (JP); Tamihide Yasumoto, Kawasaki (JP)

(73) Assignee: Fujitsu Semiconductor Limited, Yokohama (JP)

( * ) Notice: Subject to any disclaimer, the term of this patent is extended or adjusted under 35 U.S.C. 154(b) by 159 days.

(21) Appl. No.: 11/501,755

(22) Filed: Aug. 10, 2006

(65) Prior Publication Data

US 2007/0035726 A1 Feb. 15, 2007

Related U.S. Application Data

(63) Continuation-in-part of application No. 11/287,314, filed on Nov. 28, 2005, now abandoned.

(30) Foreign Application Priority Data

Aug. 11, 2005 (JP) ............................ 2005-233644
Mar. 20, 2006 (JP) ............................ 2006-077573

(51) Int. Cl.
*G01N 21/88* (2006.01)
*G01F 9/00* (2006.01)

(52) U.S. Cl. .................... 356/237.4; 356/243.4; 430/5

(58) Field of Classification Search ... 356/237.2–237.5, 356/234.1, 243.4, 243.6
See application file for complete search history.

(56) References Cited

U.S. PATENT DOCUMENTS

| | | | | |
|---|---|---|---|---|
| 4,386,850 A * | 6/1983 | Leahy | ..................... | 356/243.4 |
| 5,387,971 A * | 2/1995 | Koashi et al. | ................ | 356/246 |
| 6,038,019 A * | 3/2000 | Chang et al. | .............. | 356/237.3 |
| 6,050,125 A * | 4/2000 | Geyer et al. | ................... | 73/1.01 |
| 6,411,378 B1 * | 6/2002 | Pike | ........................ | 356/237.5 |
| 6,583,870 B2 * | 6/2003 | Noda | ....................... | 356/237.5 |
| 6,901,160 B2 * | 5/2005 | Chapman et al. | ............ | 382/141 |
| 6,911,284 B2 * | 6/2005 | Rettenmaier et al. | ........... | 430/5 |
| 7,193,698 B2 * | 3/2007 | Lin et al. | ................. | 356/237.3 |
| 2003/0194820 A1 * | 10/2003 | Jakatdar et al. | ............... | 438/16 |
| 2005/0041850 A1 * | 2/2005 | Watkins et al. | .............. | 382/145 |
| 2005/0168730 A1 * | 8/2005 | Sakai et al. | .............. | 356/237.4 |
| 2007/0265797 A1 * | 11/2007 | Nishiyama et al. | .......... | 702/128 |

* cited by examiner

FOREIGN PATENT DOCUMENTS

JP 7-120404 A 5/1995

OTHER PUBLICATIONS

Irby, J., Kinosky, D., Hsu, T., Qian, R., Mahajan, A., Thomas, S., Anthony, B., Banerjee, S., Tasch, A., and Magee, C. 1992. In situ B-doped Si epitaxial films grown at 450° C. by remote plasma enhanced chemical vapor deposition: physical and electrical characterization. J. Electron. Mater. 21, 5 (May 1992), 543-547.*

*Primary Examiner*—Gregory J Toatley, Jr.
*Assistant Examiner*—Rebecca C Slomski
(74) *Attorney, Agent, or Firm*—Westerman, Hattori, Daniels & Adrian, LLP

(57) ABSTRACT

A reference substrate for defect detection sensitivity calibration has: patterns and programmed defective portions which are cone defects with different sizes and are formed at random on a silicon substrate. By using the reference substrate for defect detection sensitivity calibration, it is possible to obtain an index, usable in manufacturing management, for determining sensitivity adjustment after a lamp is replaced in an illumination part of a defect inspection apparatus.

21 Claims, 20 Drawing Sheets

FIG. 5

| FOCUS OFFSET | LAMP A | CONE DEFECT | FOREIGN SUBSTANCE | OTHERS |
|---|---|---|---|---|
| −0.6 | 42 | 13 | 8 | 21 |
| −0.4 | 114 | 69 | 9 | 35 |
| −0.3 | 170 | 123 | 9 | 37 |
| −0.2 | 243 | 187 | 9 | 46 |
| −0.1 | 273 | 219 | 9 | 44 |
| 0.0 | 303 | 245 | 9 | 48 |
| 0.1 | 302 | 247 | 9 | 45 |
| 0.2 | 276 | 225 | 9 | 41 |
| 0.3 | | | | |
| 0.4 | 143 | 105 | 7 | 31 |
| 0.5 | | | | |
| 0.6 | 39 | 14 | 7 | 18 |

BEFORE PERIODIC REPLACEMENT OF LAMP

1746/wf

AFTER PERIODIC REPLACEMENT OF LAMP

1757/wf

BEFORE PERIODIC REPLACEMENT OF LAMP

301/wf

AFTER PERIODIC REPLACEMENT OF LAMP

303/wf

BEFORE PERIODIC REPLACEMENT OF LAMP

1636/wf

AFTER PERIODIC REPLACEMENT OF LAMP

1500/wf

DEFECT INSPECTION APPARATUS, SENSITIVITY CALIBRATION METHOD FOR THE SAME, SUBSTRATE FOR DEFECT DETECTION SENSITIVITY CALIBRATION, AND MANUFACTURING METHOD THEREOF

CROSS-REFERENCE TO RELATED APPLICATIONS

This is a continuation-in-part application of application Ser. No. 11/287,314, filed Nov. 28, 2005.

This application is based upon and claims the benefit of priority from the prior Japanese Patent Application Nos. 2005-233644, filed on Aug. 11, 2005, and 2006-077573, filed on Mar. 20, 2006, the entire contents of which are incorporated herein by reference.

BACKGROUND OF THE INVENTION

1. Field of the Invention

The present invention relates to a defect inspection apparatus inspecting a defect on a substrate, a sensitivity calibration method for the same, a substrate for defect detection sensitivity calibration that is used for calibrating detection sensitivity of a defect detection apparatus, and a manufacturing method thereof.

2. Description of the Related Art

In manufacturing a semiconductor device, it is necessary to inspect the occurrence of a defect such as a so-called cone defect. The cone defect is formed when a semiconductor substrate is etched due to a foreign substance adhering on the substrate or is etched due to a foreign substance during processes of forming various kinds of patterns. In accordance with the recent progress of the miniaturization of a system LSI circuit, in order to detect more microscopic defects, the wavelength of an illumination light used in a defect inspection apparatus targeted at a semiconductor device under the design rule of, for example, a 65 nm to 90 nm size is becoming still shorter. This has given rise to a problem that it becomes difficult to determine the proper optimization of sensitivity.

Conventionally, there has been proposed a reference substrate for defect detection sensitivity calibration. In the reference substrate for defect detection sensitivity, programmed foreign substance portions that are highly discriminatable are regularly formed (see a patent document 1). This substrate is used for discriminating (judging) the quality of the detection sensitivity of a defect inspection apparatus for foreign substance inspection or of an appearance inspection apparatus.

[Patent Document 1] Japanese Patent Application Laid-open No. Hei 7-120404

In the reference substrate for defect detection sensitivity calibration as proposed in the patent document 1, programmed defective portions are provided as a regular pattern, and the heights of the programmed defective portions are adjusted to a constant value of 50 nm to 200 nm. On the other hand, in a chip area on an actual semiconductor substrate, complicated semiconductor elements and wiring patterns different in size are densely formed. Therefore, even when defect detection using the reference substrate for defect detection sensitivity calibration as proposed in the patent document 1 detects a large number of microscopic defects, it is difficult to appropriately cope with a case where an unexpected change occurs in the defect inspection apparatus. Concretely, in actual semiconductor processes, when a light source (for example, a laser light source, a lamp, or the like) is replaced in an illumination part of the defect inspection apparatus, the number of detected microscopic defects changes to a relatively great extent. However, there is a problem that the defect inspection using the reference substrate for defect detection sensitivity calibration as described in the patent document 1 cannot fully ensure defect detection sensitivity.

SUMMARY OF THE INVENTION

The present invention was made in view of the above-described problem, and it is an object thereof to provide a defect inspection apparatus, a sensitivity calibration method for the same, a substrate for defect detection sensitivity calibration, and a manufacturing method thereof which are capable of sufficiently ensuring defect detection sensitivity high enough to detect microscopic defects occurring in actual semiconductor processes and, in particular, which are capable of providing an index, usable in manufacturing management, for determining sensitivity adjustment after a light source is replaced in an illumination part of the defect inspection apparatus.

A substrate for defect detection sensitivity calibration of the present invention is a substrate for defect detection sensitivity calibration used for calibrating detection sensitivity of a defect detection apparatus detecting a defective portion occurring in a device, the substrate including: a defect formation portion; a pattern portion provided on a surface of the defect formation portion and having a predetermined pattern; and a plurality of programmed defective portions formed on the surface of the defect formation portion, wherein the programmed defective portions are formed to have arbitrary sizes.

A manufacturing method of a substrate for defect detection sensitivity calibration of the present invention is a manufacturing method of a substrate for defect detection sensitivity calibration used for calibrating detection sensitivity of a defect detection apparatus detecting a defective portion formed in a device, the method comprising: depositing a material film for forming a predetermined pattern on a surface of a defect formation portion; forming a pattern portion having the pattern by processing the material film; and forming programmed defective portions with arbitrary sizes by processing the surface of the defect formation portion, with an arbitrary plural number of particles, which are part of the material film adhering to the surface of the substrate, functioning as a mask.

A sensitivity calibration method for a defect inspection apparatus of the present invention is a sensitivity calibration method for a defect inspection apparatus which performs defect inspection by using a substrate for defect detection sensitivity calibration and by irradiating the substrate for defect detection sensitivity calibration with light from an illumination part to detect the light reflected on the substrate for defect detection sensitivity calibration, wherein the substrate for defect detection sensitivity calibration includes: a defect formation portion; a pattern portion provided on a surface of the defect formation portion and having a predetermined pattern; and a plurality of programmed defective portions with arbitrary sizes formed on the surface of the defect formation portion, and the method including: detecting the programmed defective portions in the substrate for defect detection sensitivity calibration before the light source is replaced; detecting the programmed defective portions in the substrate for defect detection sensitivity calibration after the light source is replaced; and calculating a difference between the number of the programmed defective portions detected before the replacement of the light source and the number of the programmed defective portions detected after the replacement of the light source, and by using the calculated value, performing an adjustment work of making the number of the programmed defective portions detected after the replacement of the light source equal to the number of the programmed defective portions detected before the replacement of the light source.

A defect inspection apparatus of the present invention includes: a substrate for defect detection sensitivity calibration that includes a defect formation portion; a pattern portion provided on a surface of the defect formation portion and having a predetermined pattern and a plurality of programmed defective portions with arbitrary sizes formed on the surface of the defect formation portion; an illumination part having a light source and irradiating the substrate for defect detection sensitivity calibration with light; a detecting unit detecting the light reflected on the substrate for defect detection sensitivity calibration; a counting unit counting the number of the programmed defective portions, which are detected by the detecting unit, on the substrate for defect detection sensitivity calibration; and a calculating unit which calculates a difference between the number of the programmed defective portions detected before the light source is replaced and the number of the programmed defective portions detected after the light source is replaced.

BRIEF DESCRIPTION OF THE DRAWINGS

FIG. 5 is a characteristic chart showing the relation between the focus offset amount and the number of the detected defects in a focus curve;

DETAILED DESCRIPTION OF THE PREFERRED EMBODIMENTS

Basic Gist of the Present Invention

The present inventor thought that in order to obtain an index for determining sensitivity adjustment after a light source of an illumination part is replaced, a substrate having microscopic defects similar to those occurring in actual semiconductor processes has to be used as a sample substrate for defect detection. Therefore, as the sample substrate, prepared was a substrate having microscopic pseudo (programmed) defects with random sizes imitating those occurring in the actual semiconductor processes. Using this substrate, the number of defects was detected before and after the replacement of the light source (a lamp here) of the illumination part. Specifically, as will be described later, the substrate used as the sample substrate has on a surface thereof contingently formed programmed defective portions with arbitrary sizes.

Figure 1:
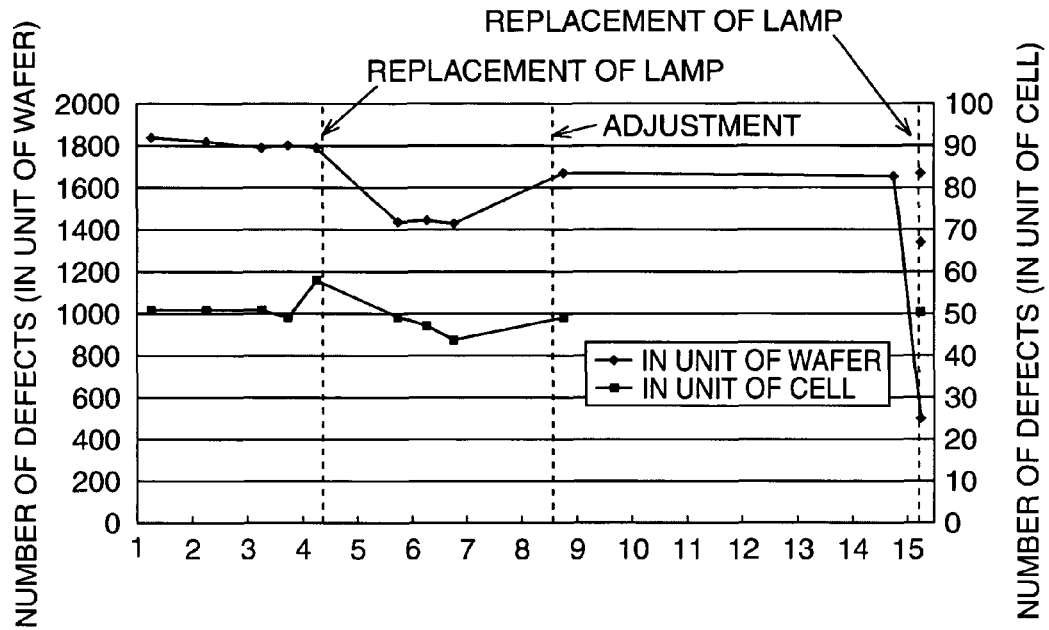
FIG. 1 is a characteristic chart showing results when the number of defects is detected before and after a lamp is replaced by using, as a sample substrate, a substrate having microscopic programmed defects with random sizes.

FIG. 1 shows results of the defect detection using this sample substrate. In FIG. 1, the inspection date (here, a relative value is shown, and one graduation corresponds to, for example, two days) is taken on the horizontal axis and the number of defects is taken on the vertical axis. Here, the number of defects in the whole substrate (in a unit of a wafer) and the number of defects in a predetermined area in the substrate (in a unit of a cell) were examined by using the same substrate.

It is seen from FIG. 1 that the number of defects detected after the replacement of the lamp greatly decreases. As a comparison, the number of defects was detected before and after the replacement of the lamp by using the reference substrate for defect detection sensitivity calibration as described in the patent document 1. Results of the detection showed, though not given in the drawing, that there was no difference between the both. This means that a change in detection sensitivity of the defect detection apparatus ascribable to the replacement of the lamp cannot be recognized when the reference substrate for defect detection sensitivity calibration as described in the patent document 1 is used.

Figure 2:
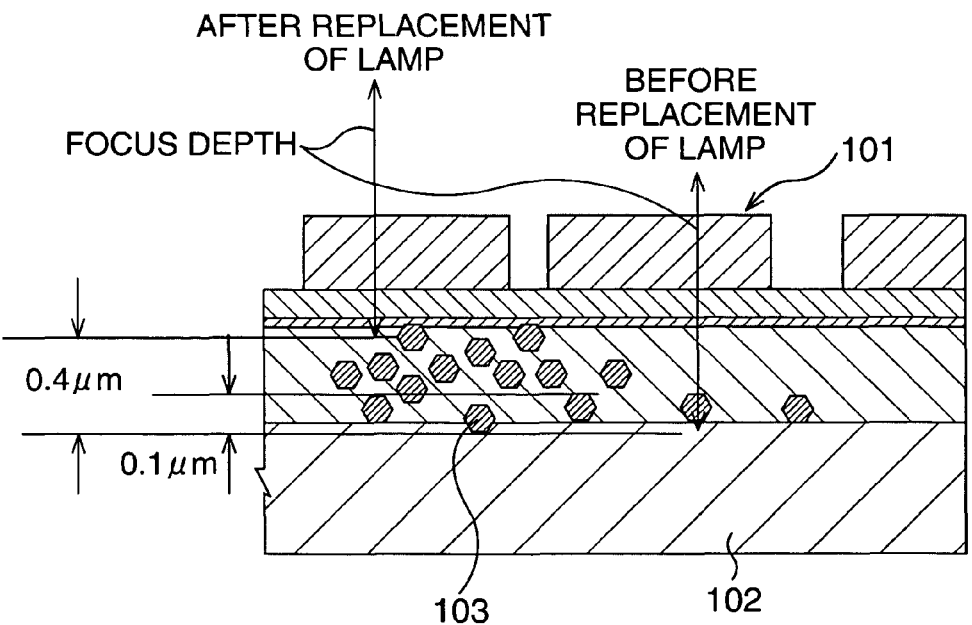
FIG. 2 is a rough cross-sectional view to illustrate a change in focus after the replacement of the lamp relative to a focus before the replacement of the lamp.

A possible change occurring in the defect inspection apparatus side due to the replacement of the lamp is, for example, a focus change. The focus change is caused by a shift of an optical axis of the illumination part after the replacement of the lamp from an optical axis before the replacement of the lamp. Specifically, as shown in FIG. 2, if microscopic defects (mainly cone defects 103) occur in a silicon substrate 102 on which an actual pattern (actual wiring pattern or the like) is formed, the random cone defects 103 that are positioned at height, for example, within 400 nm (0.4 μm) can be detected before the replacement of the lamp. However, after the replacement of the lamp, the focus shifts upward, so that the cone defects 103 that are positioned at height of, for example, 400 nm or less cannot be detected.

Figure 3:
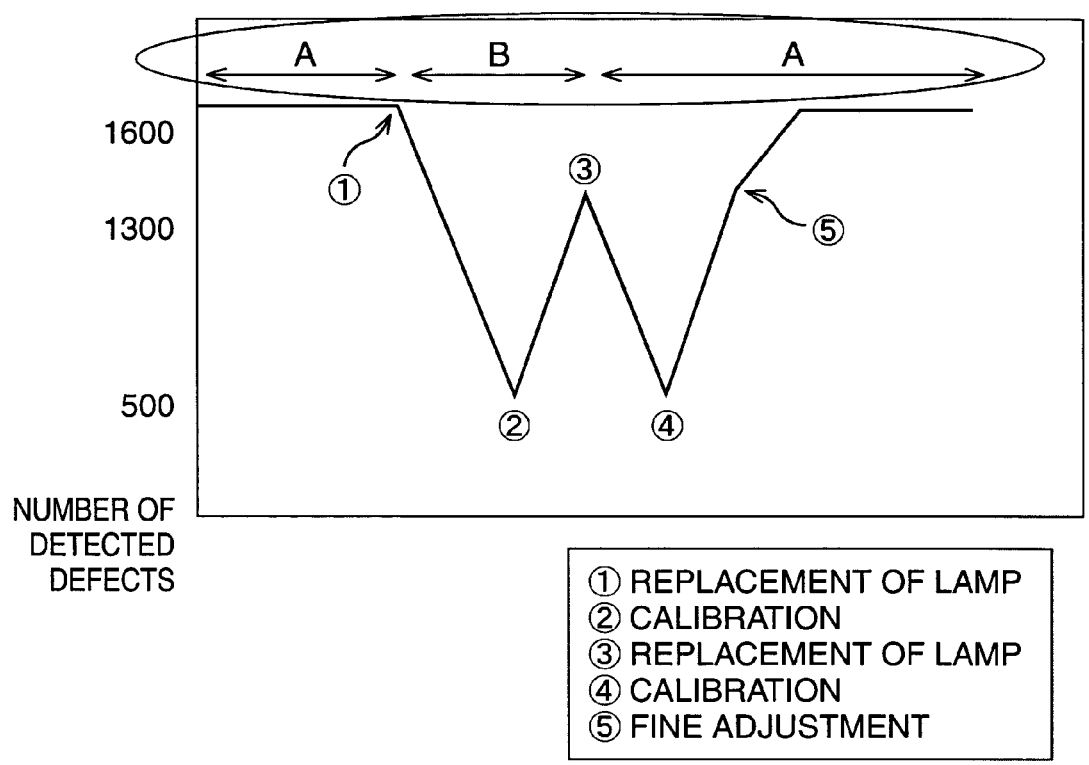
FIG. 3 is an explanatory chart showing an example where the focus change caused by the replacement of the lamp is calibrated.

FIG. 3 shows an example where the above-described sample substrate is used and the focus change caused by the replacement of the lamp is calibrated. The calibration of the focus change is a series of works consisting of an apparatus adjustment work, which includes the correction of the optical axis and so on (calibration), and subsequent fine adjustment. In FIG. 3, defect detection was first carried out by using a lamp A. Subsequently, (1) the lamp A was replaced by another new lamp B. At this time, a considerable decrease in the number of detected defects was seen. Subsequently, (2) as a result of calibration, the number of detected defects came close to the original value obtained when the lamp A was used. Subsequently, (3) the lamp B was again replaced by the lamp A. At this time, a considerable decrease in the number of detected defects substantially on the same level as that in (1) was seen again. Then, as a result of subsequent calibration, the number of detected defects came close to the number of the original value obtained when the lamp A was used, similarly to (2). Then, (5) as a result of fine adjustment, the number of detected defects became equal to the original value obtained when the lamp B was used. A series of these results can lead to the following conclusion. That is, the change in the number of the detected defects after the replacement of the lamp relative to that before the replacement of the lamp is not ascribable to the deterioration or the like of the lamps A, B but is ascribable to the focus change due to the deviation of the optical axes or the like of the lamps A, B.

Figure 4:
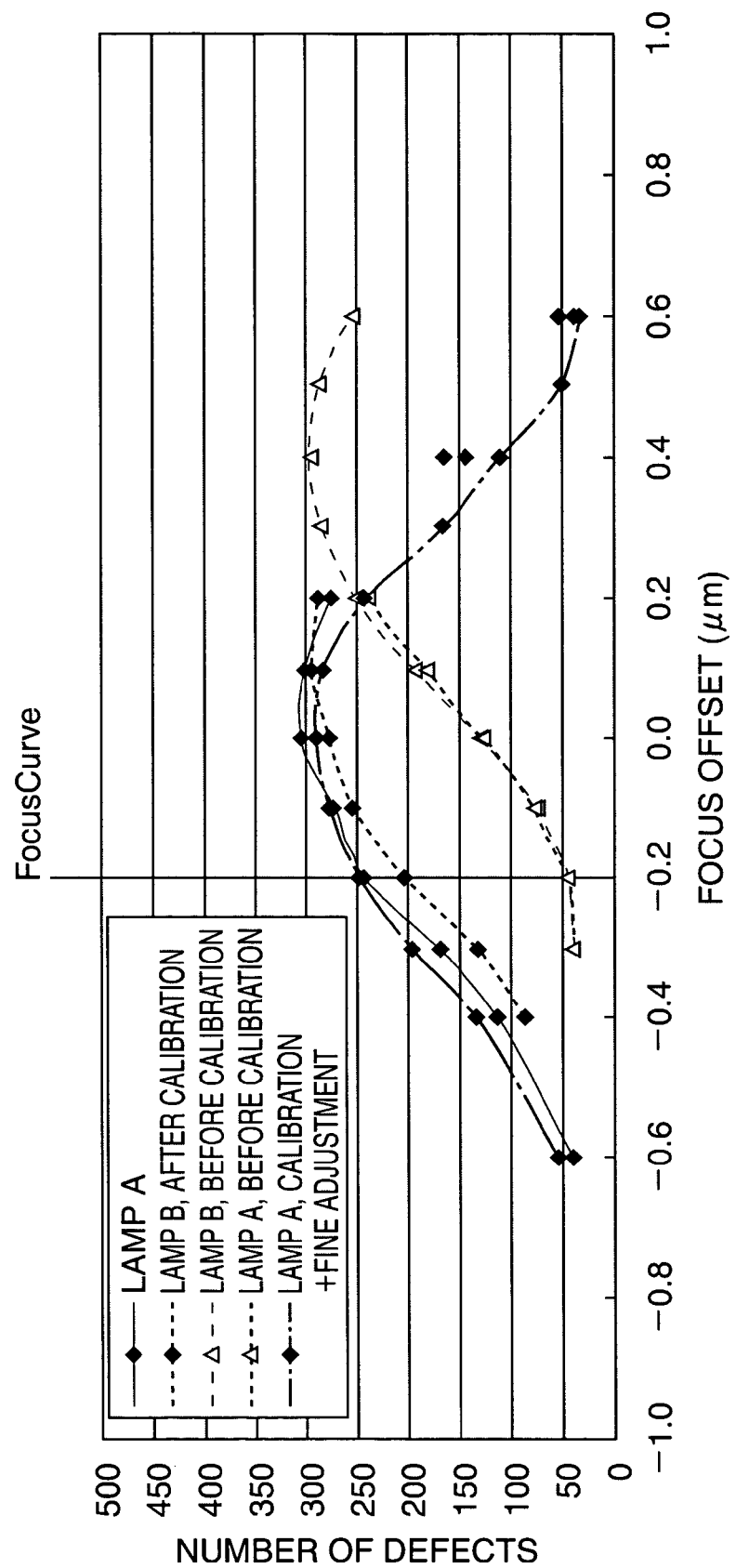
FIG. 4 is a characteristic chart showing results of studies on the relation between a focus offset amount and the number of detected defects.

FIG. 4 shows results of studies on the relation between a focus offset amount and the number of detected defects regarding the series of processes shown in FIG. 3. It is seen that the focus curve obtained when the lamp A is used for the defect detection and the focus curve obtained when the fine adjustment in the above-described (5) is made substantially match each other. FIG. 5 is a table showing the relation between the focus offset amount and the number of the detected defects in the focus curve obtained when the lamp A is used for the defect detection. The focus offset amount is set to, for example, −0.2 μm according to a recipe in the defect detection apparatus, and it is seen from FIGS. 4A, 4B and FIG. 5 that the peak of the actual focus offset is near 0.0 μm.

The above-described studies have led to the following conclusion. That is, for example, the use of a substrate in which a plurality of programmed defective portions with different sizes (heights or the like) are randomly formed on a surface thereof as in the actual semiconductor processes makes it possible to accurately recognize a deviation amount of the focus offset ascribable to the replacement of the lamp. Based on this deviation amount of the focus offset, it is possible to perform accurate calibration (calibration and fine adjustment) of the focus change. This calibration is intended for adjusting the focus offset to the optimum value, thereby making the number of the detected defects after the replacement of the lamp equal to that before the replacement of the lamp as soon as possible. Incidentally, among defects occurring in the actual semiconductor processes, about 80% of the total number of various kinds of defects are so-called cone defects. Therefore, forming the programmed defective portions on the reference substrate for defect detection sensitivity calibration as the cone defects has no problem.

Concrete Embodiment of the Present Invention

Based on the above-described basic gist of the present invention, a concrete embodiment to which the present invention is applied will be hereinafter described in detail with reference to the drawings.

First Embodiment

Figure 6A:
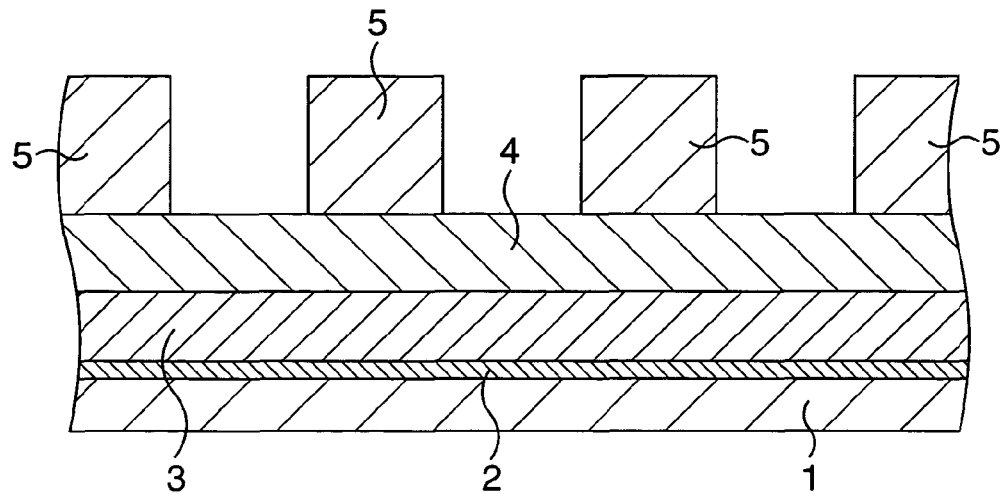
FIG. 6A to FIG. 6C are rough cross-sectional views showing, in the order of steps, a manufacturing method of a reference substrate for defect detection sensitivity calibration according to a first embodiment.
Figure 6B:
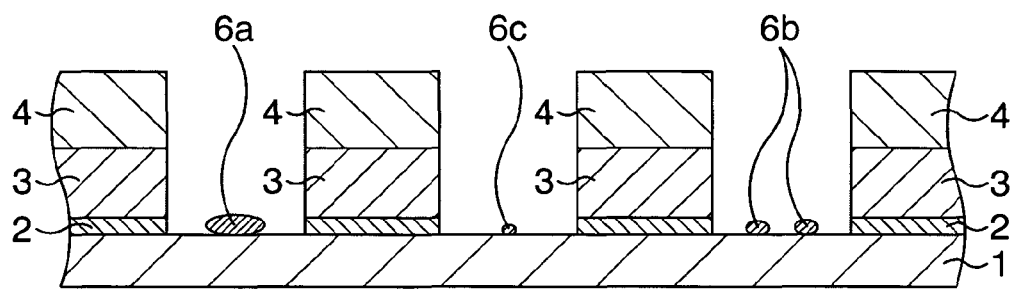
Figure 6C:
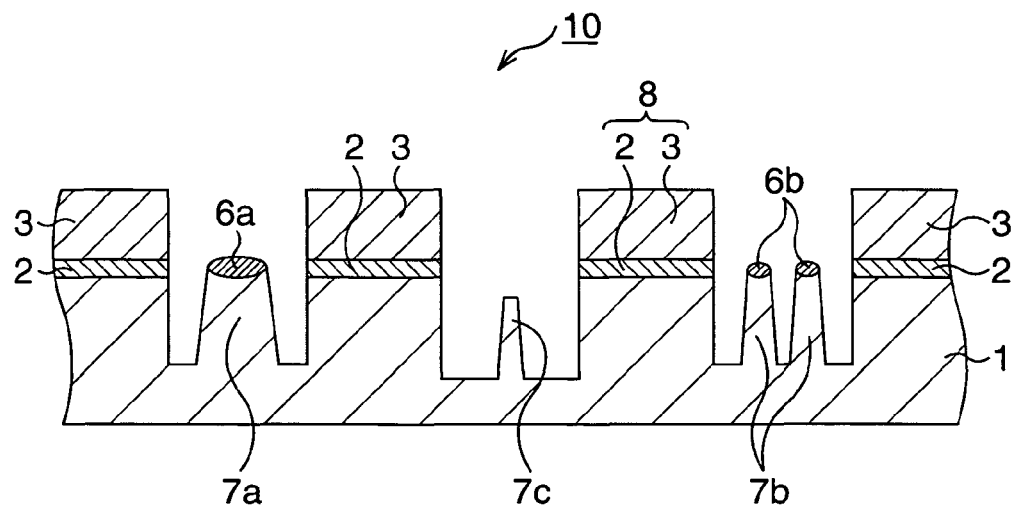

FIG. 6A to FIG. 6C are rough cross-sectional views showing, in the order of steps, a manufacturing method of the reference substrate for defect detection sensitivity calibration according to a first embodiment.

First, as shown in FIG. 6A, a silicon oxide film 2 with an about 10 nm to 50 nm thickness is formed on a surface of a semiconductor substrate, for example, a silicon substrate 1 by, for example, a CVD method or a thermal oxidation method. Next, a silicon nitride film 3 with an about 100 nm to 200 nm thickness is formed on the silicon oxide film 2 by, for example, a CVD method. Next, a polycrystalline silicon film 4 with an about 100 nm to 200 nm thickness is formed on the silicon nitride film 3 by, for example, a CVD method. Then, a resist is applied on the polycrystalline silicon film 4, and the resist is processed by lithography to form a resist pattern 5.

Subsequently, as shown in FIG. 6B, using the resist pattern 5 as a mask and the silicon substrate 1 as a stopper, the polycrystalline silicon film 4, the silicon nitride film 3, and the silicon oxide film 2 are dry-etched. FIG. 6B shows an example of a state where the resist pattern 5 has been removed by etching in the course of the dry etching. By this dry etching, the polycrystalline silicon film 4, the silicon nitride film 3, and the silicon oxide film 2 are-patterned in the shape of the resist pattern 5, and part of silicon oxide scattering at the time of the etching of the silicon oxide film 2 turns to particles 6 to adhere to the surface of the exposed silicon substrate 1. The particles 6 contingently and randomly scatter, so that they adhere both to dense and sparse areas of the patterned structure. The particles 6 are randomly formed and thus come to have contingently arbitrary sizes. Here, particles 6a, 6b, 6c are shown as examples of the particles 6 in the descending order of their sizes.

Subsequently, as shown in FIG. 6C, using the polycrystalline silicon film 4 as a mask and the silicon nitride film 3, for example, as a stopper, the whole surface is dry-etched. At this time, the polycrystalline silicon film 4 is etched to disappear. A surface layer of the silicon substrate 1 is also etched. In this etching, the particles 6 adhering on the surface of the silicon substrate 1 function as masks. As a result, linear (or block) patterns 8 in each of which the silicon nitride film 3 is stacked on the silicon oxide film 2 are formed, and programmed defective portions 7 being cone defects in a conical shape are formed in the silicon substrate 1 to which the particles 6 adhere. In this manner, a reference substrate 10 for defect detection sensitivity calibration of this embodiment is completed. By the etching in which the randomly formed particles 6a, 6b, 6c with contingently arbitrary sizes function as masks, programmed defective portions 7a, 7b, 7c as the programmed defective portions 7 with contingently arbitrary sizes (heights) are formed, similarly to microscopic defects occurring in a silicon substrate in actual semiconductor processes.

In this embodiment, it is preferable to adjust the thickness of the silicon oxide film 2, the distance between the patterns 8, and the like, in consideration of a target to be inspected by the defect inspection apparatus. This adjustment is made so that the sizes of the programmed defective portions 7 have values equal to or smaller than ten times a value of a dimension of the linear patterns 8, for example, arbitrary values within a range from 80 nm to 200 nm. Here, the size of the programmed defective portion 7c is smaller than the sizes of the programmed defective portions 7a, 7b. This is because the particle 6c disappears in the course of the etching due to its extremely minute size and patterning without any mask follows thereafter.

Figure 7:
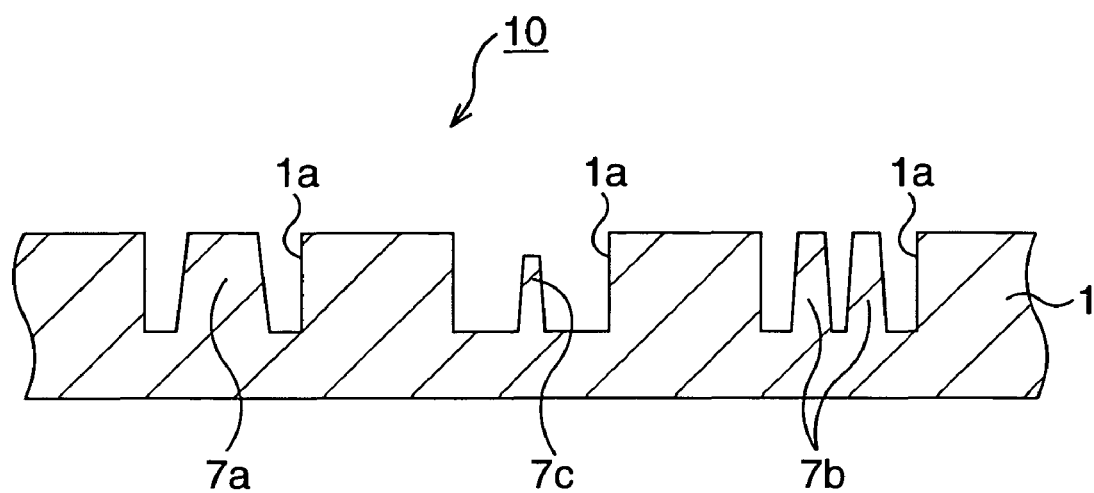
FIG. 7 is a rough cross-sectional view showing another example of the reference substrate for defect detection sensitivity calibration according to the first embodiment.

Here, as shown in FIG. 7, the linear patterns 8 may be removed by wet etching or the like. FIG. 7 shows, as an example, a state where the particles 6a, 6b are also removed by the wet etching or the like Removing the linear patterns 8 produces a state in which grooves 1a are formed in the surface of the silicon substrate 1 and only the programmed defective portions 7a to 7c remain in the grooves 1a. This substrate becomes the reference substrate for defect detection sensitivity calibration with uniform refractive index on the surface of the substrate.

Figure 8:
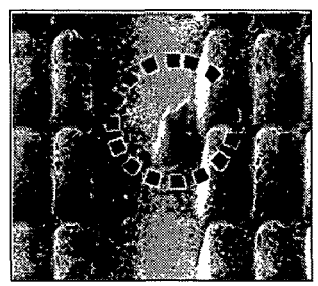
FIG. 8 is a view showing a micrograph of a state of part of a surface of the reference substrate for defect detection sensitivity calibration.

FIG. 8 shows a micrograph of a state of part of the surface of the reference substrate for defect detection sensitivity calibration manufactured through the processes in FIG. 6A to FIG. 6C. Here, the inner areas surrounded by the broken-line circles are the programmed defective portions 7, which are formed near the patterns 8. In a case where predetermined wiring patterns and element patterns are formed by actual semiconductor processes, if such cone defects occur near, for example, the wiring patterns, these defects would be so-called killer defects fatal to the semiconductor element.

Next, a rough structure of the defect detection apparatus according to this embodiment will be described with reference to FIG. 9.

This defect detection apparatus includes the reference substrate 10 for defect detection sensitivity calibration described above, an illumination part 21 including a lamp 21a as a light source and irradiating the programmed defective portions 7 of the reference substrate 10 for defect detection sensitivity calibration with light from the lamp 21a, a detector 22 detecting reflection (scattered) light reflected (scattered) on the programmed defective portions 7, a counter 23 counting the number of the programmed defective portions 7 recognized by the detector 22 (the number of detected defects), and a calculator 24 calculating a difference between two numerical values.

Here, the calculator 24 calculates a difference between the number of the programmed defective portions 7 detected by the detector 22 and counted by the counter 23 (the number of detected defects) before the lamp 21a of the illumination part 21 is replaced and the number of detected defects detected by the detector 22 and counted by the counter 23 after the lamp 21a is replaced. The calculator 24 provides the calculated difference as a change value of the number of detected defects after the replacement of the lamp 21a relative to that before the replacement of the lamp 21a. This change value is used in an adjustment work (the above-described calibration of the focus change). In the adjustment work, the number of the programmed defective portions 7 detected after the replacement of the lamp 21a is made equal to the number of the programmed defective portions 7 detected before the replacement of the lamp 21a.

Here, the calculator 24 may display the plural numbers of the detected defects subsequently detected by the detector 22 and counted by the counter 23 before the replacement of the lamp 21a of the illumination part 21. This enables the recognition of the number of defects suggesting that the lamp 21a has no deterioration. Another suitable configuration is such that, for example, the calculator 24 calculates the number of defects suggesting that the lamp 21a before being replaced has no deterioration.

A sensitivity calibration method for the defect detection apparatus in FIG. 9 will be described with reference to FIG. 10.

In periodic defect inspection using the reference substrate 10 for defect detection sensitivity calibration, the counter 23 counts the number of detected defects of the substrate 10 for defect detection sensitivity calibration before the lamp 21a is replaced (for example, at a predetermined time immediately before the replacement) (Step S1). Here, the plural numbers of the detected defects counted by the counter 23 before the replacement of the lamp 21a may be displayed. This enables the recognition of the number of defects suggesting that the lamp 21a has no deterioration. Another suitable configuration is such that the calculator 24 calculates the number of defects suggesting that the lamp 21a has no deterioration. If the number of defects suggesting that the lamp 21a has no deterioration has been thus recognized, this serves as an index for judging, for example, before the replacement of the lamp 21a that the lamp 21a has deterioration if the numbers of detected defects at a plurality of measured points have values lower to a certain extent than the aforesaid number of defects suggesting that the lamp 21a has no deterioration.

Subsequently, the counter 23 counts the number of detected defects of the substrate 10 for defect detection sensitivity calibration after the replacement of the lamp 21a (for example, at a predetermined time immediately after the replacement) (Step S2).

Subsequently, the calculator 24 calculates a difference between the number of the detected defects of the substrate 10 for defect detection sensitivity calibration before the replacement of the lamp 21a and the number of the detected defects of the substrate 10 for defect detection sensitivity calibration after the replacement of the lamp 21a (Step S3). Here, if the number of defects as the index of no deterioration of the lamp 21a before the replacement of the lamp 21a has been recognized, a difference between this number of defects and the number of the detected defects of the substrate 10 for defect detection sensitivity calibration after the replacement of the lamp 21a is calculated. The calculated value is used in the adjustment work (the above-described calibration of the focus change) in which the number of the programmed defective portions 7 detected after the replacement of the lamp 21a is made equal to the number of the programmed defective portions 7 detected before the replacement of the lamp 21a.

Figure 11:
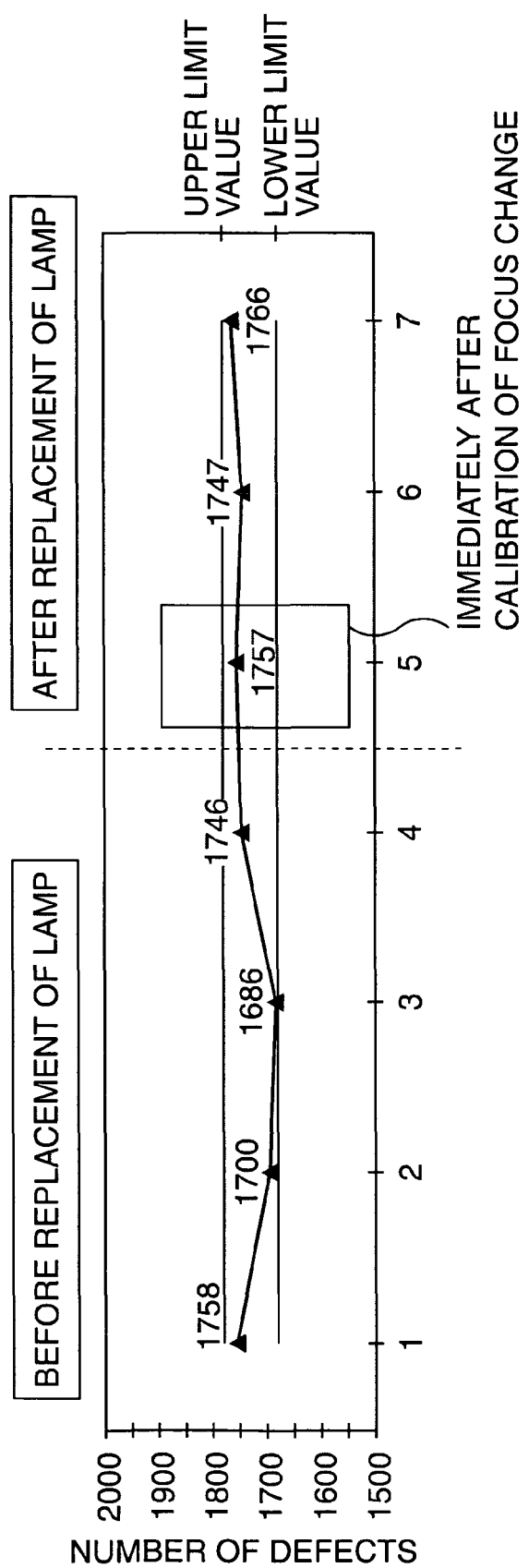
FIG. 11 is a characteristic chart showing an example of a change in the number of detected defects when sensitivity of the defect detection apparatus is actually calibrated.
Figure 12A:
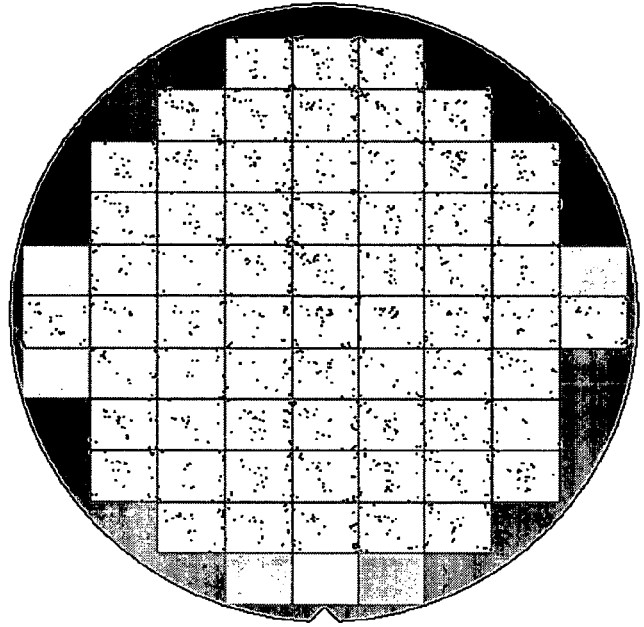
FIG. 12A and FIG. 12B are rough plane views showing the distribution of the number of the detected defects in the substrate and showing the comparison between defect detection in the substrate for defect detection sensitivity calibration immediately before the replacement of the lamp and that immediately after the calibration of the focus change.
Figure 12B:
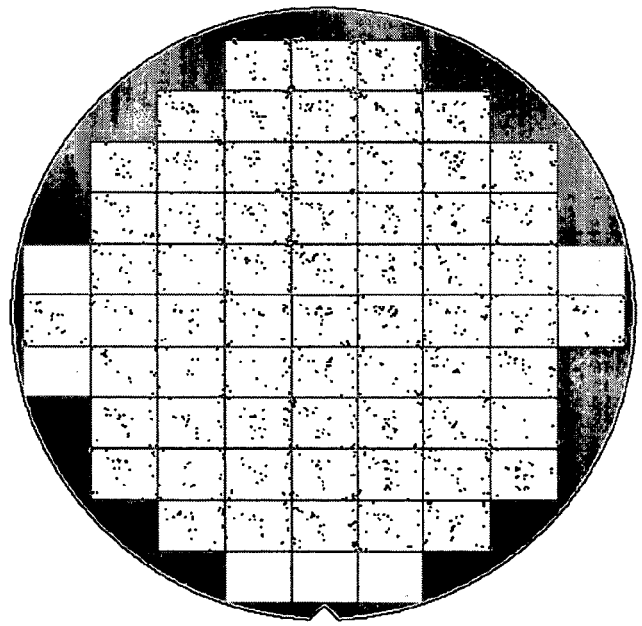
Figure 13:
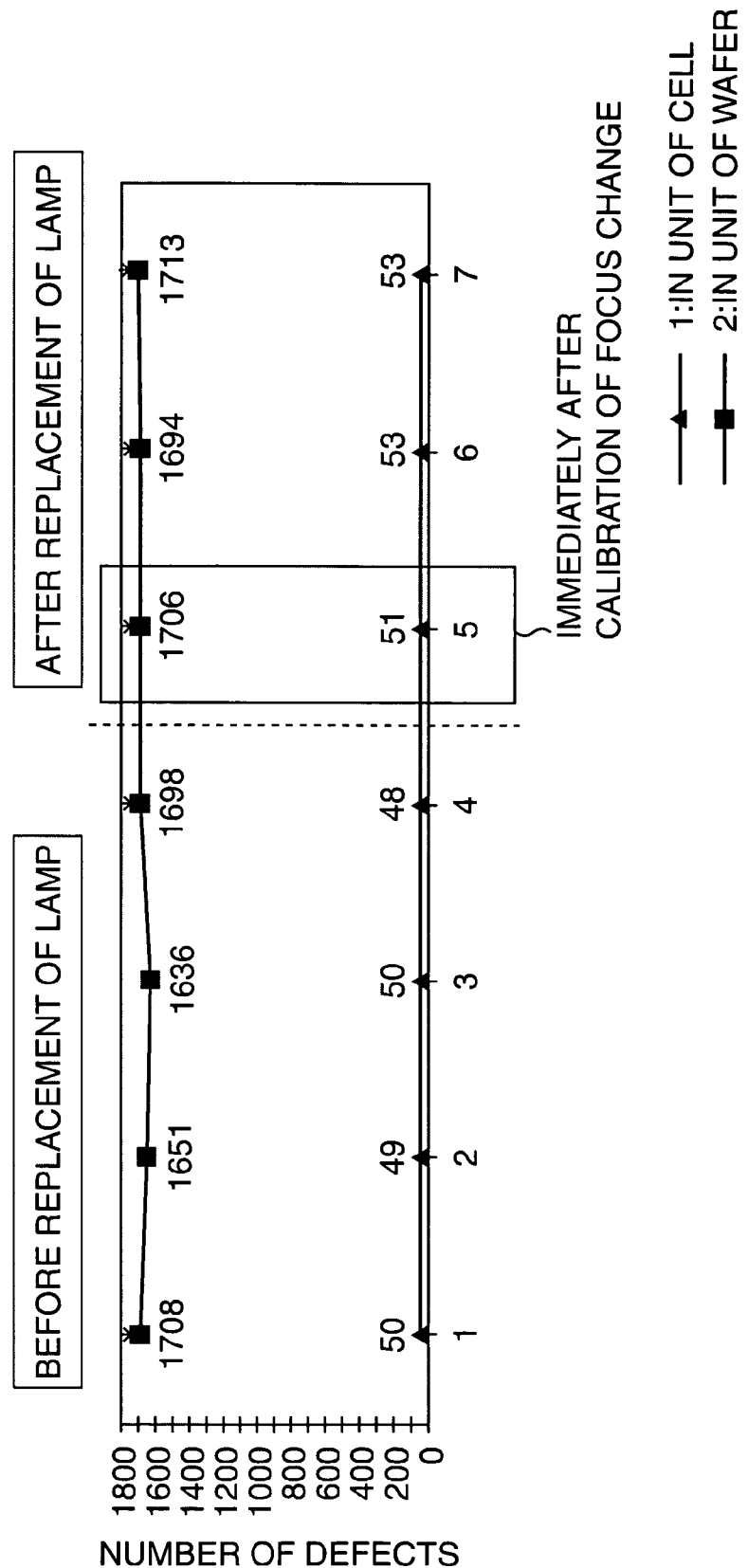
FIG. 13 is a characteristic chart showing an example of changes in the number of detected defects in the whole substrate (in a unit of a wafer) and in the number of detected defects in a predetermined area (in a unit of a cell) in the substrate.

FIG. 11 shows an example of the change in the number of detected defects when the sensitivity of the defect detection apparatus is actually calibrated by the above-described sensitivity calibration method. FIG. 12A and FIG. 12B show the distribution of the number of the detected defects in the substrate and also show the comparison between defect detection in the substrate 10 for defect detection sensitivity calibration immediately before the replacement of the lamp 21a and that immediately after the calibration of the focus change. Further, FIG. 13 shows an example of changes in the number of detected defects in the whole substrate (in a unit of a wafer) and in the number of detected defects in a predetermined area having the programmed defective portions in the substrate (in a unit of a cell) when the sensitivity of the defect detection apparatus is actually calibrated by the above-described sensitivity calibration method.

In FIG. 11, the horizontal axis shows the period of the defect detection (seven days in the shown example) and the vertical axis shows the number of detected defects. The numerical value surrounded by the rectangle is the number of detected defects immediately after the lamp 21a is replaced and the focus change is calibrated. In FIG. 11 and FIGS. 12A, 12B, the number of detected defects before the replacement of the lamp 21a is 1746 and the number of detected defects immediately after the calibration of the focus change is 1757, and thus it can be said that these numbers are substantially equal. Further, in FIG. 13, in a unit of a wafer, the number of detected defects before the replacement of the lamp 21a is 1698 and the number of detected defects immediately after the calibration of the focus change is 1706. In a unit of a cell, the number of detected defects before the replacement of the lamp 21a is 48, and the number of detected defects immediately after the calibration of the focus change is 51. Therefore, both in a unit of a wafer and in a unit of a cell, it can be said that the values before and after the replacement of the lamp 21a are substantially equal. Moreover, in FIG. 11, the numbers of detected defects subsequently obtained before and after the replacement of the lamp 21a fall within a prescribed allowable range (between the upper limit value and the lower limit value in the drawing). Therefore, applying the above-described sensitivity calibration method to the sensitivity calibration for the defect detection apparatus can ensure high sensitivity of the defect detection apparatus both before and after the replacement of the lamp 21a.

Figure 14:
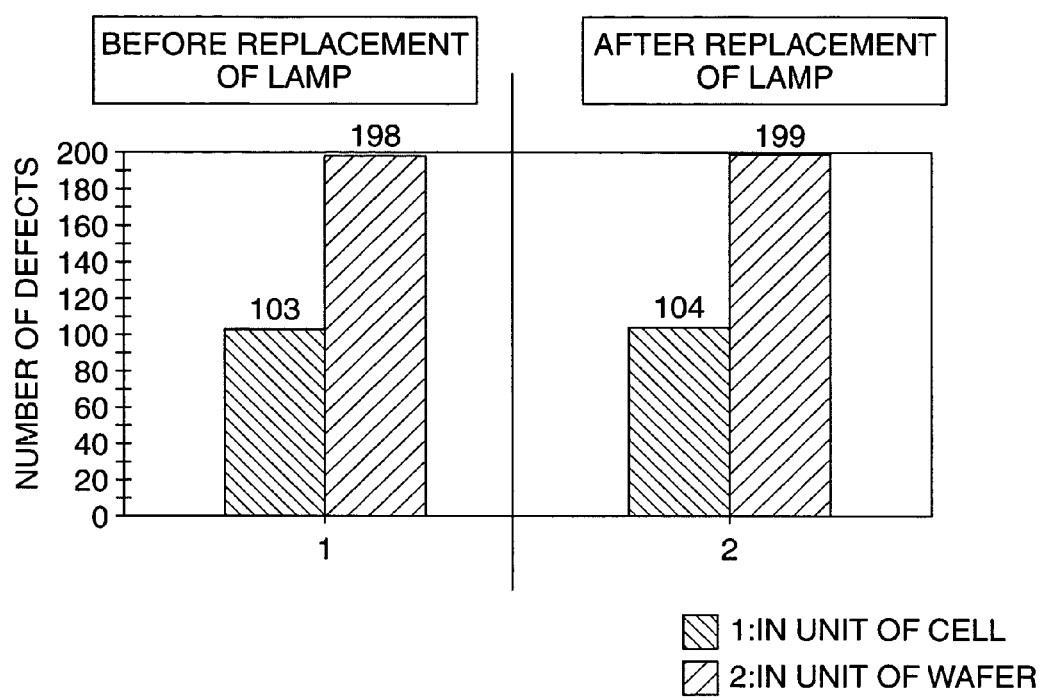
FIG. 14 is a characteristic chart showing an example of changes in the number of detected defects when the sensitivity of the defect detection apparatus is actually calibrated by using a substrate having a gate pattern.
Figure 15A:
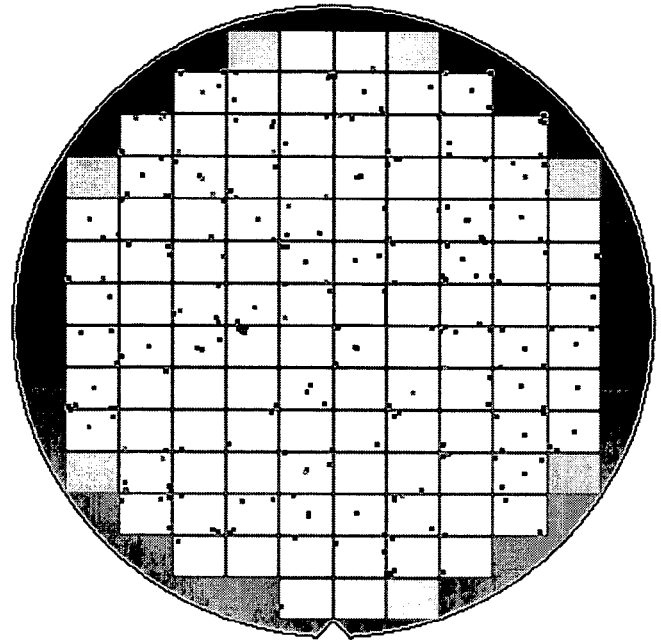
FIG. 15A and FIG. 15B are rough plane views showing the distribution of the number of the defects in the substrate detected by using the substrate having the gate pattern, FIG. 15A showing the total number of defects in a unit of a wafer and in a unit of a cell before the replacement of the lamp, and FIG. 15B showing the total number of the same after the replacement of the lamp.
Figure 15B:
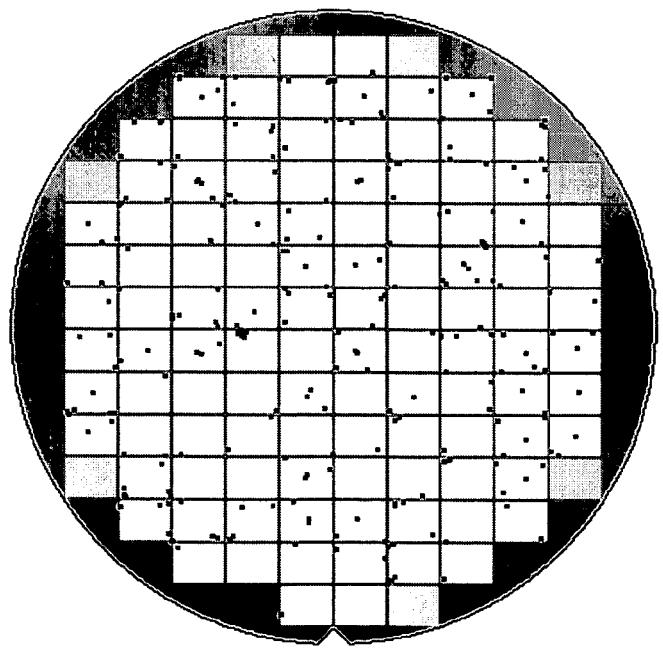

Further, it was studied how the number of detected defects changes after the replacement of the lamp 21a relative to that before the replacement of the lamp 21a. In the study, a substrate having an actual gate pattern was used as the sample substrate, instead of the substrate 10 for defect detection sensitivity calibration. FIG. 14 and FIGS. 15A, 15B show the results. FIG. 14 shows how the number of detected defects in the whole substrate (in a unit of a wafer) and the number of detected defects in a predetermined area (in a unit of a cell) change after the replacement of the lamp 21a relative to those before the replacement of the lamp 21a. FIGS. 15A, 15B show the distribution of the number of detected defects in the substrate, FIG. 15A showing the total number of detected defects in a unit of a wafer and in a unit of a cell before the replacement of the lamp 21a, and FIG. 15B showing the total number of the same after the replacement of the lamp 21a. Note that the sample substrate used here does not have any influence of the cone defects and thus the number of detected defects thereof becomes a relatively small value.

In FIG. 14, in a unit of a wafer, the number of detected defects before the replacement of the lamp 21a is 198 and the number of detected defects immediately after the calibration of the focus change is 199. In a unit of a cell, the number of detected defects before the replacement of the lamp 21a is 103 and the number of detected defects immediately after the calibration of the focus change is 104.

Therefore, it can be said that, both in a unit of a wafer and in a unit of a cell, the values before and after the replacement of the lamp 21a are substantially equal. Further, the study on the total number of the detected defects in a unit of a wafer and in a unit of a cell as in FIGS. 15A, 15B shows the same result.

Therefore, applying the above-described sensitivity calibration method to the sensitivity calibration of the defect detection apparatus can ensure high sensitivity of the defect detection apparatus both before and after the replacement of the lamp 21a even when a substrate on which various patterns, typically, gate patterns are formed, is used instead of the sample substrate.

Figure 16:
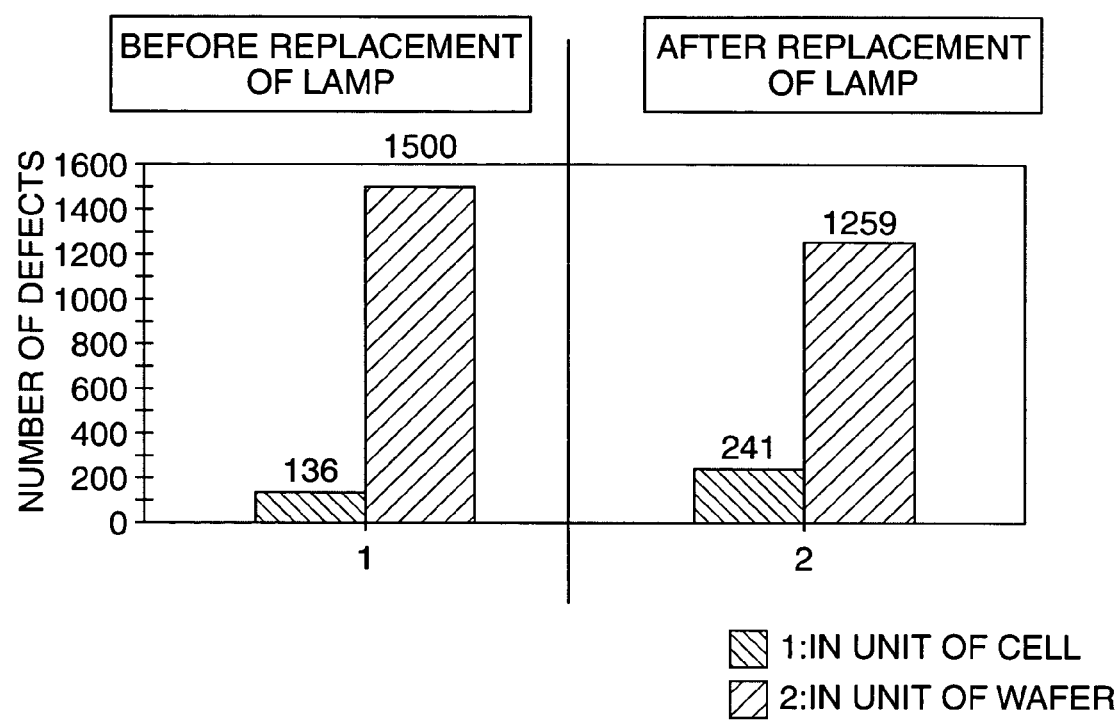
FIG. 16 is a characteristic chart showing changes in the number of detected defects in the whole substrate (in a unit of a wafer) and in the number of detected defects in a predetermined area (in a unit of a cell) in the substrate after the replacement of the lamp, relative to those before the replacement of the lamp.
Figure 17A:
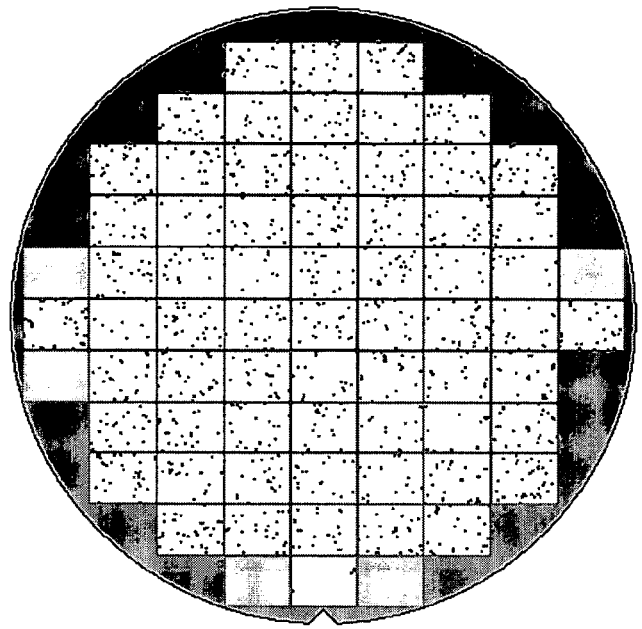
FIG. 17A and FIG. 17B are rough plane views showing the distribution of the number of the detected defects before and after the replacement of the lamp, FIG. 17A showing the total number of detected defects in a unit of a wafer and in a unit of a cell before the replacement of the lamp and FIG. 17B showing the total number of the same after the replacement of the lamp.
Figure 17B:
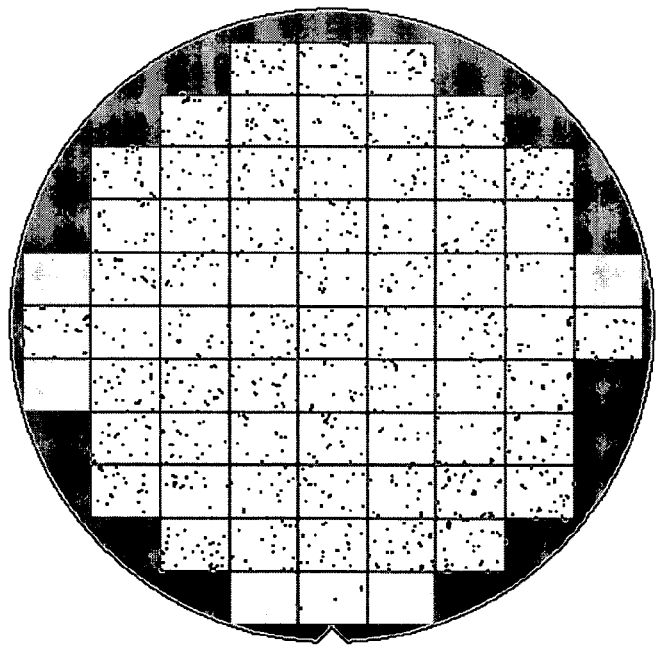

It was further studied how the number of detected defects changes at the time which is after the replacement of the lamp 21a but before the calibration of the focus change, relative to the number of detected defects before the replacement of the lamp 21a. In a substrate used here as a sample substrate, a Cu material for forming a Cu wiring by a so-called damascene method has undergone CMP processing. FIG. 16 and FIGS. 17A, 17B show the results. FIG. 16 shows how the number of detected defects in the whole substrate (in a unit of a wafer) and the number of detected defects in a predetermined area (in a unit of a cell) in the substrate change after the replacement of the lamp 21a, relative to those before the replacement of the lamp 21a. FIGS. 17A, 17B show the distribution of the number of the detected defects in the substrate before and after the replacement of the lamp 21a, FIG. 17A showing the total number of the detected defects in a unit of a wafer and in a unit of a cell before the replacement of the lamp 21a, and FIG. 17B showing the total number of the same after the replacement of the lamp 21a. Note that the sample substrate used here has minute flaws on its surface due to the CMP processing and thus the number of detected defects becomes a relatively large value.

In FIG. 16, in a unit of a wafer, the number of the detected defects before the replacement of the lamp 21a is 1500 and the number of the detected defects immediately after the calibration of the focus change is 1259. In a unit of a cell, the number of the detected defects before the replacement of the lamp 21a is 136 and the number of the detected defects immediately after the calibration of the focus change is 241. Thus, both in a unit of a wafer and in a unit of a cell, the change is seen immediately after the calibration of the focus change, relative to the number of the detected defects before the replacement of the lamp 21a. The study on the total number of the detected defects in a unit of a wafer and in a unit of a cell as in FIGS. 17A, 17B shows the same result. It has been confirmed that these changes become scarcely observable when the focus change is calibrated after the replacement of the lamp 21a.

Figure 18:
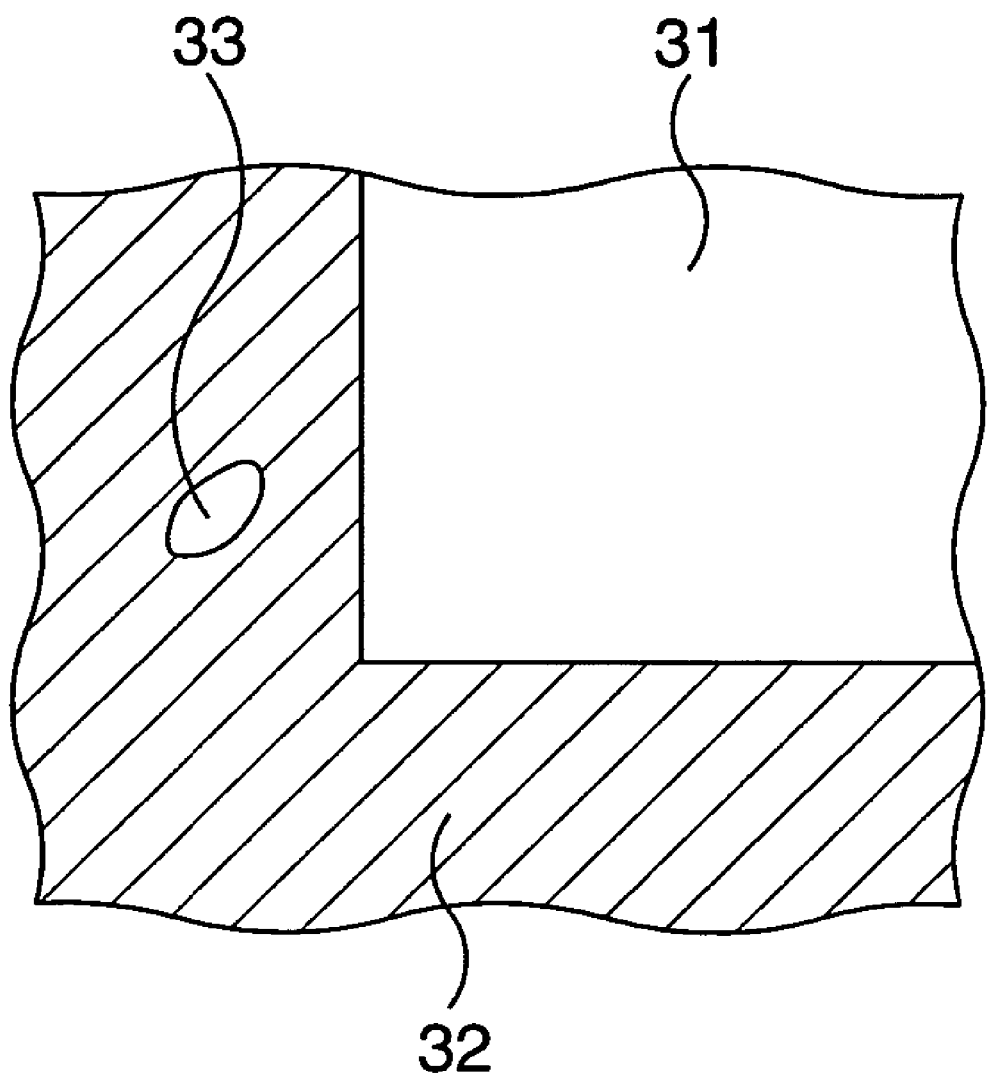
FIG. 18 is a rough plane view showing a state where a void is produced in part of an insulator of a STI element isolation structure.

As has been described hitherto, according to this embodiment, it is possible to sufficiently ensure the defect detection sensitivity high enough to detect minute defects occurring in actual semiconductor processes and in particular, it is possible to provide an index, usable in manufacturing management, for determining sensitivity adjustment after the lamp 21a is replaced in the illumination part 21 of the defect inspection apparatus. For example, when a void 103 with an about 80 nm to 200 nm size occurs in part of an insulator of a STI element isolation structure 102 that demarcates an active region 101 on a semiconductor substrate as shown in FIG. 18, a conventional method might not be able to detect the defect. In this embodiment, even after the lamp 21a is replaced, such a microscopic defect (the void 103 can be a killer defect) can be detected without fail.

Figure 9:
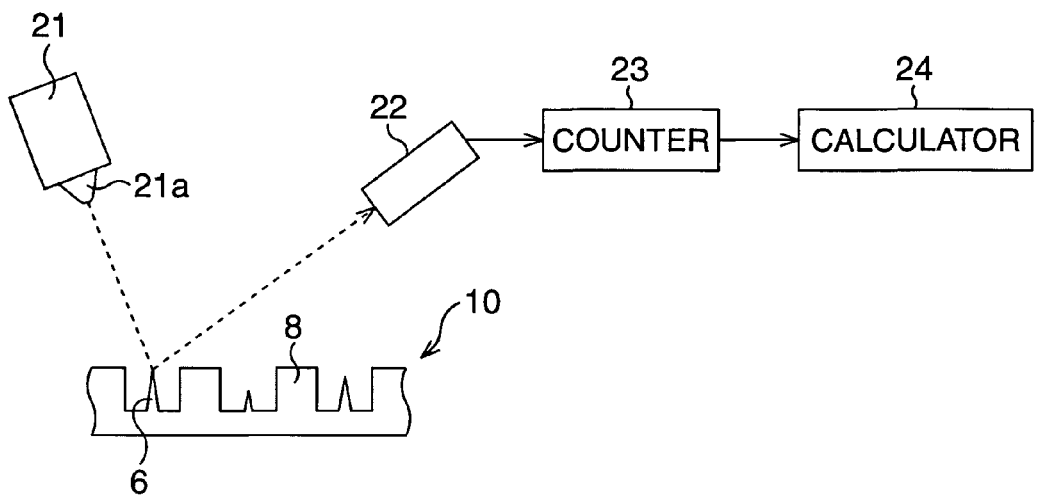
FIG. 9 is a schematic view showing a rough structure of a defect detection apparatus according to the first embodiment.

The functions of the respective constituent elements (the counter 23, the calculator 24, and so on excluding the illumination part 21 and the detector 22 in FIG. 9) constituting the defect detection apparatus according to the above-described embodiment are realizable by the operation of a program stored in a RAM, a ROM, or the like of a computer. Likewise, the steps (Steps S1 to S3 and so on in FIG. 10) of the defect detection method are realizable by the operation of the program stored in the RAM or the ROM of the computer. The program and a computer-readable storage medium in which the program is recorded are included in the present invention.

Concretely, the abovementioned program is supplied to the computer from a recording medium such as, for example, a CD-ROM in which the program is recorded or via various kinds of transmission media. Examples, other than the CD-ROM, usable as the recording medium recording the program are a flexible disk, a hard disk, a magnetic tape, a magneto-optical disk, a nonvolatile memory card, and the like. As the transmission medium of the program, usable is a communication medium in a computer network system for propagating program information as a carrier wave to supply the program information. Here, the computer network is a LAN, a WAN such as the Internet, a wireless communication network, or the like, and the communication medium is a wired circuit such as an optical fiber, a wireless circuit, or the like.

Further, it is to be understood that the program included in the present invention is not limited to a program realizing the functions of the above-described embodiment by being supplied to and executed by the computer. For example, a program realizing the functions of the above-described embodiment by operating with an OS (operating system), other application software, or the like running on the computer is also included in the present invention. Further, in a case where the functions of the above-described embodiment are realized by causing a function expansion board or a function expansion unit of the computer to execute part or all of the supplied program, the program is also included in the present invention.

Figure 19:
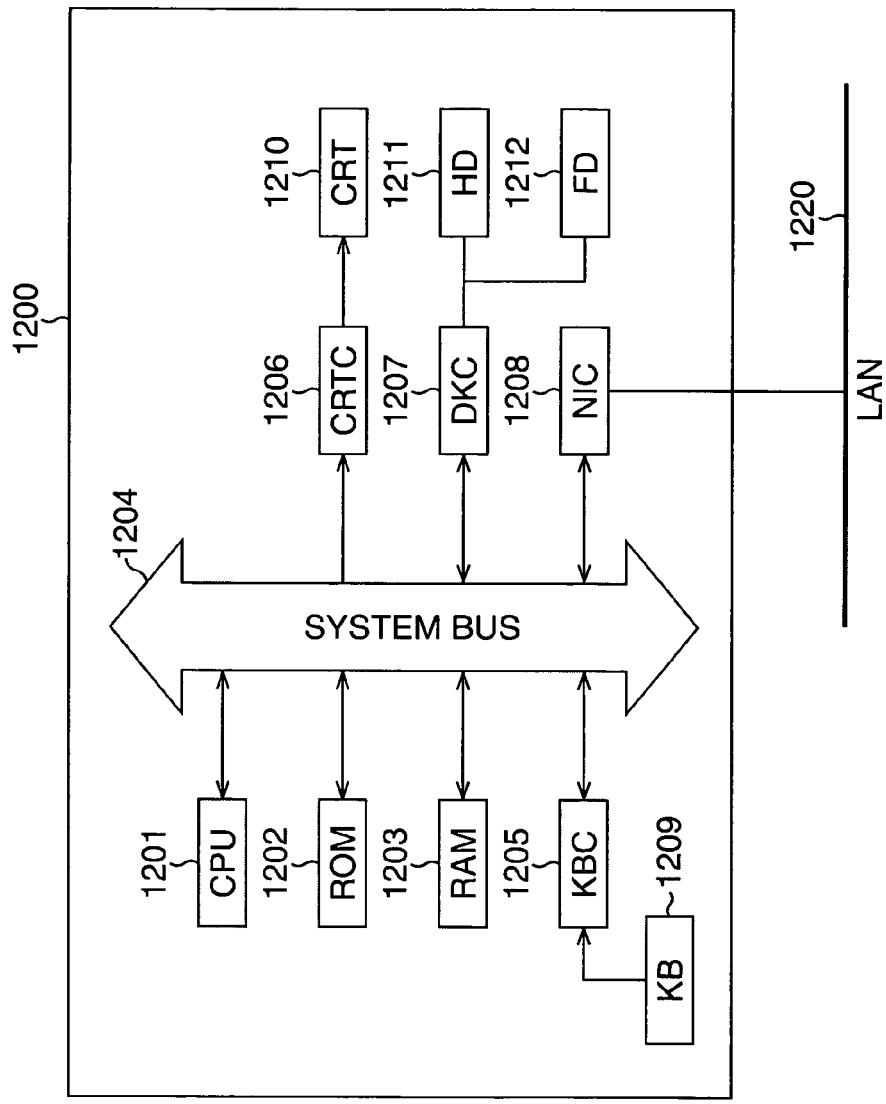
FIG. 19 is a schematic diagram showing an internal structure of a personal user terminal apparatus.

For example, FIG. 19 is a schematic diagram showing the internal structure of a personal user terminal apparatus. In FIG. 19, reference numeral 1200 denotes a personal computer (PC) including a CPU 1201. The PC 1200 executes device control software stored in a ROM 1202 or a hard disk (HD) 1211 or supplied from a flexible disk drive (FD) 1212. The PC 1200 centrally controls devices connected to a system bus 1204.

Figure 10:
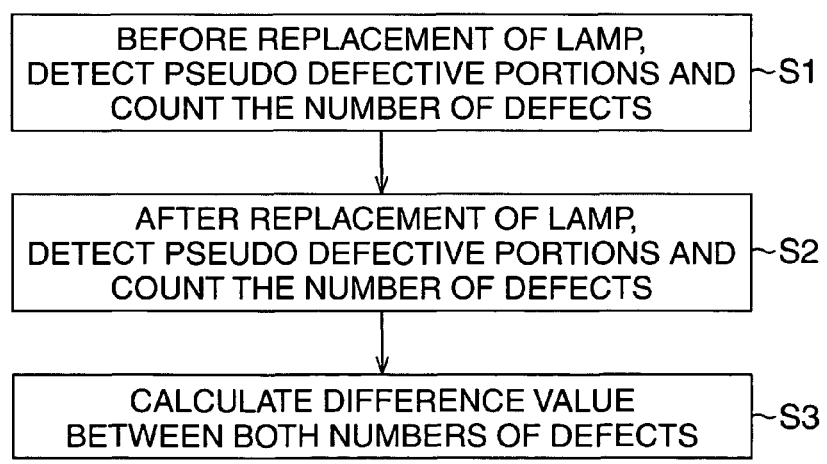
FIG. 10 is a flowchart showing a sensitivity calibration method for the defect detection apparatus.

The procedure of Steps S1 to S3 and so on in FIG. 10 of the embodiment is realized by a program stored in the CPU 1201, the ROM 1202, or the hard disk (HD) 1211 of the PC 1200.

Reference numeral 1203 denotes a RAM that functions as a main memory, a work area, and the like of the CPU 1201. Reference numeral 1205 denotes a keyboard controller (KBC) that controls command input from a keyboard (KB) 1209, not-shown devices, and so on.

Reference numeral 1206 denotes a CRT controller (CRTC) that controls the display of a CRT display (CRT) 1210. Reference numeral 1207 denotes a disk controller (DKC). The DKC 1207 controls accesses to the hard disk (HD) 1211 and the flexible disk (FD) 1212 storing a boot program, a plurality of applications, an edit file, a user file, a network management program, and the like. Here, the boot program is a startup program, that is, a program for starting the execution (operation) of hardware and software of a personal computer.

Reference numeral 1208 denotes a network interface card (NIC) that enables bidirectional data exchange with a network printer, other network's equipment, or other PCs via a LAN 1220.

MODIFICATION EXAMPLE

Here, a modification example of the first embodiment will be described.

This example is slightly different from the first embodiment in the structure of a reference substrate for defect detection sensitivity calibration. Concretely, a defect formation portion being a portion where programmed defective portions are formed is not on a silicon substrate but on an upper film thereof.

Figure 20A:
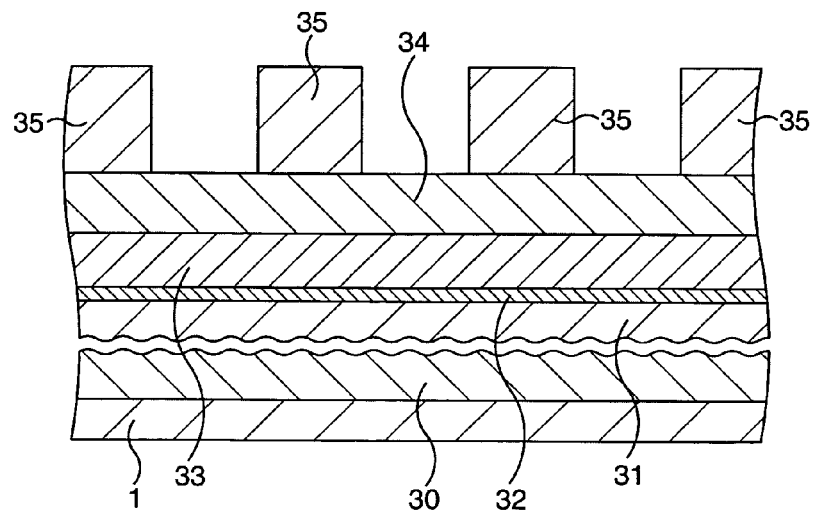
FIG. 20A to FIG. 20C are rough cross-sectional views showing, in the order of steps, a manufacturing method of a reference substrate for defect detection sensitivity calibration according to a modification example of the first embodiment.
Figure 20B:
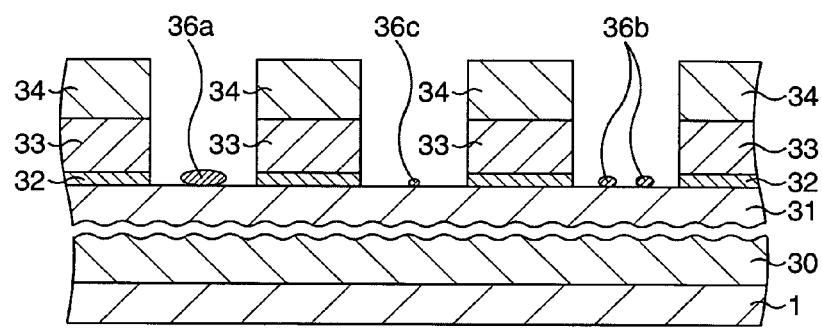
Figure 20C:
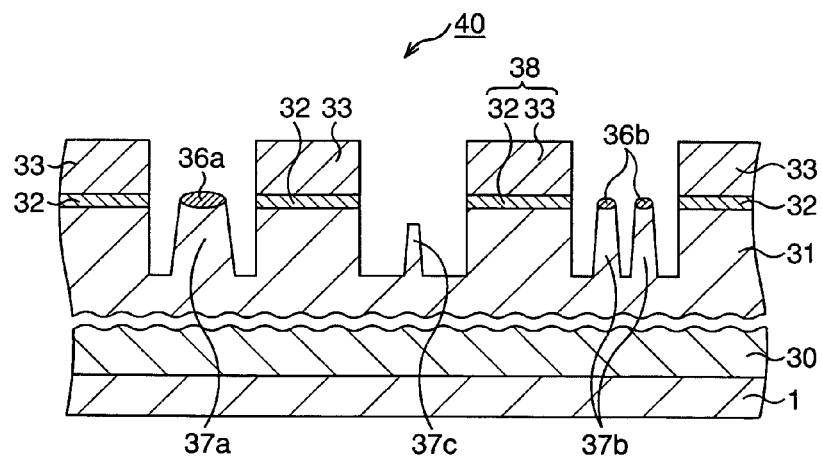

FIGS. 20A to 20C are rough cross-sectional views showing, in the order of steps, a manufacturing method of a reference substrate for defect detection sensitivity calibration according to the modification example of the first embodiment.

First, as shown in FIG. 20A, a polycrystalline silicon film 31 is formed by, for example, a CVD method above a semiconductor substrate, for example, a silicon substrate 1 via an interlayer insulation film 30 and so on. Next, a silicon oxide film 32 with a thickness of about 10 nm to about 50 nm is formed on the polycrystalline silicon film 31 by, for example, a CVD method. Next, a silicon nitride film 33 with a thickness of about 100 nm to about 200 nm is formed on the silicon oxide film 32 by, for example, a CVD method. Next, a polycrystalline silicon film 34 with a thickness of about 100 nm to about 200 nm is formed on the silicon nitride film 33 by, for example, a CVD method. Then, a resist is applied on the polycrystalline silicon film 34 and this resist is processed by lithography to form a resist pattern 35.

Subsequently, as shown in FIG. 20B, using the resist pattern 35 as a mask and the polycrystalline silicon film 31 as a stopper, the polycrystalline silicon film 34, the silicon nitride film 33, and the silicon oxide film 32 are dry-etched. FIG. 20B shows an example of a state where the resist pattern 35 has been removed by etching in the course of the dry etching. By this dry etching, the polycrystalline silicon film 34, the silicon nitride film 33, and the silicon oxide film 32 are patterned in the shape of the resist pattern 35 and part of silicon oxide scattering at the time of the etching of the silicon oxide film 32 turns to particles 36 to adhere to a surface of the exposed polycrystalline silicon film 31. The particles 36 contingently and randomly scatter, so that they adhere to both dense and sparse areas of the patterned structure. The particles 36 are randomly formed and thus come to have contingently arbitrary sizes. Here, particles 36a, 36b, 36c are shown as examples of the particles 36 in the descending order of their sizes.

Subsequently, as shown in FIG. 20C, using the polycrystalline silicon film 34 as a mask and, for example, the silicon nitride film 33 as a stopper, the whole surface is dry-etched. At this time, the polycrystalline silicon film 34 is etched to disappear, and a surface layer of the polycrystalline silicon film 31 is also etched. In this etching, the particles 36 adhering on the surface of the polycrystalline silicon film 31 function as masks. As a result, linear (or block) patterns 38 in each of which the silicon nitride film 33 is stacked on the silicon oxide film 32 are formed, and programmed defective portions 37 being cone defects in a conical shape are formed on the polycrystalline silicon film 31 to which the particles 36 adhere. In this manner, a reference substrate 40 for defect detection sensitivity calibration of this modification example is completed.

By the etching in which the randomly formed particles 36a, 36b, 36c with contingently arbitrary sizes function as masks, programmed defective portions 37a, 37b, 37c as the programmed defective portions 37 with contingently arbitrary sizes (heights) are formed, similarly to microscopic defects occurring in a polycrystalline silicon film in actual semiconductor processes.

In this example, it is preferable to adjust the thickness of the silicon oxide film 32, the distance between the patterns 38, and the like, in consideration of a target to be inspected by the defect inspection apparatus. This adjustment is made so that the sizes of the programmed defective portions 37 have values equal to or smaller than ten times a value of a dimension of the linear patterns 38, for example, arbitrary values within a range from about 80 nm to about 200 nm. Here, the size of the programmed defective portion 37c is smaller than the sizes of the programmed defective portions 37a, 37b. This is because the particle 36c disappears in the course of the etching due to its extremely minute size and patterning without any mask follows thereafter.

Figure 21:
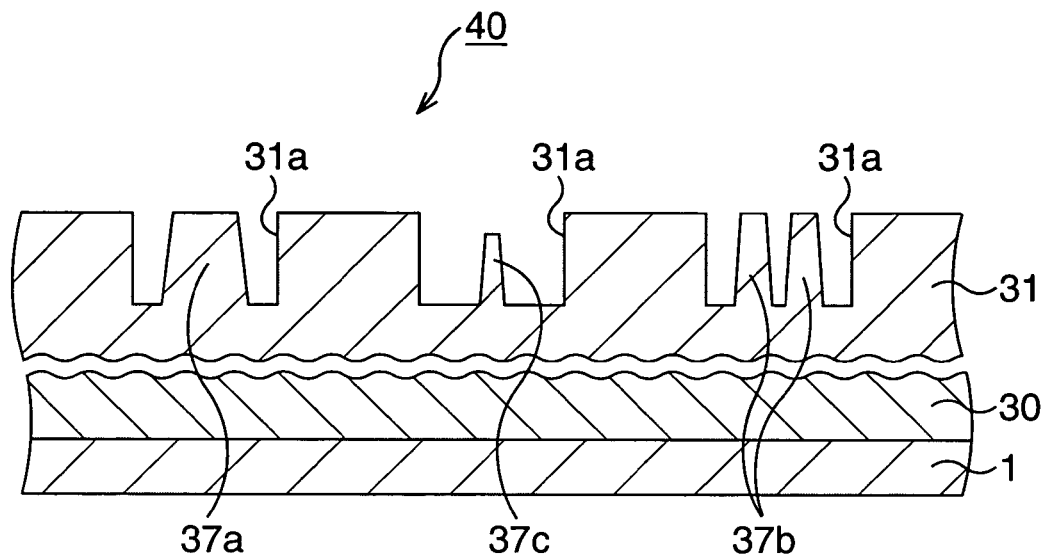
FIG. 21 is a rough cross-sectional view showing another example of the reference substrate for defect detection sensitivity calibration according to the modification example of the first embodiment.

Here, as shown in FIG. 21, the linear patterns 38 may be removed by wet etching or the like. FIG. 21 shows, as an example, a state where the particles 36a, 36b are also removed by the wet etching or the like Removing the linear patterns 38 produces a state in which grooves 31a are formed in the surface of the polycrystalline silicon film 31 and only the programmed defective portions 37a to 37c remain in the grooves 31a. This substrate becomes the reference substrate for defect detection sensitivity calibration with uniform refractive index on the surface of the polycrystalline silicon film 31.

Incidentally, this example shows an example where the programmed defective portions 37a to 37c are formed on the polycrystalline silicon film 31 formed above the silicon substrate 1, but for example, the programmed defective portions may be formed on an interlayer insulation film formed above the silicon substrate 1.

According to this example, similarly to the first embodiment, it is possible to fully ensure the defect detection sensitivity high enough to detect minute defects occurring in actual semiconductor processes, ana in particular, it is possible to provide an index, usable in manufacturing management, for determining sensitivity adjustment after the lamp 21a is replaced in the illumination part 21 of the defect detection apparatus.

Second Embodiment

This embodiment is different from the first embodiment in the structure of a reference substrate for defect detection sensitivity calibration.

Figure 22:
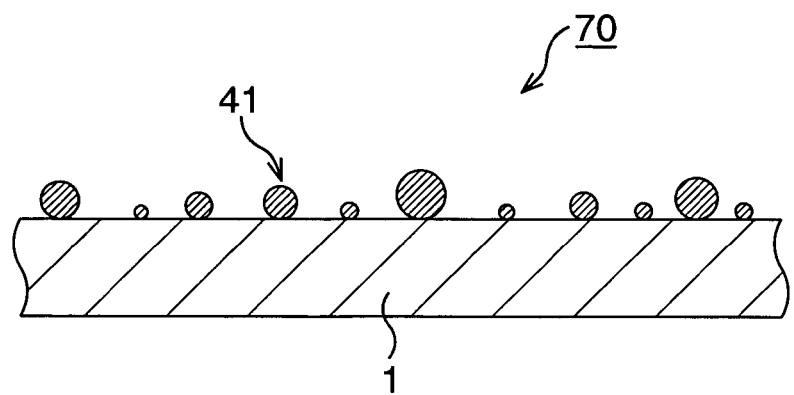
FIG. 22 is a rough cross-sectional view showing a reference substrate for defect detection sensitivity calibration according to a second embodiment.

FIG. 22 is a rough cross-sectional view showing a reference substrate for defect detection sensitivity calibration according to the second embodiment.

In this embodiment, particulates with nonuniform size are scattered on a surface of a semiconductor substrate, for example, a silicon substrate 1. These particulates function as programmed defective portions 41. Here, parts where many target defect occurrences are observed are especially selected as areas for scattering the particulates. This enables efficient sensitivity calibration.

The particulates to serve as the programmed defective portions 41 are made of, for example, silicon oxide or silicon nitride formed in particulate shape, and are scattered on the surface of the silicon substrate 1. In this embodiment, in consideration that the programmed defective portions 41 are inspection targets in a defect inspection apparatus, the size of the particulates is adjusted to any size within a range of, for example, about 80 nm to about 200 nm.

The silicon substrate 1 on whose surface the programmed defective portions 41 are thus formed by the scattering of the particulates with nonuniform size is used as a reference substrate 50 for defect detection sensitivity calibration.

According to this embodiment, the use of the reference substrate 50 for defect detection sensitivity calibration with an extremely simple structure makes it possible to fully ensure defect detection sensitivity high enough to detect minute defects occurring in actual semiconductor processes and comparable to or higher than the defect detection sensitivity of the first embodiment, and in particular, it is possible to provide an index, usable in manufacturing management, for determining sensitivity adjustment after a lamp 21a is replaced in an illumination part 21 of a defect detection apparatus.

MODIFICATION EXAMPLES

Here, modification examples of the second embodiment will be described. These modification examples are slightly different from the second embodiment in the structure of a reference substrate for defect detection sensitivity calibration. The same reference numerals and symbols are used to designate the same constituent members and so on as those of the second embodiment, and detailed description thereof will be omitted.

MODIFICATION EXAMPLE 1

In this example, a defect formation portion being a portion where programmed defective portions are formed is not on a silicon substrate but on an upper film thereof.

Figure 23A:
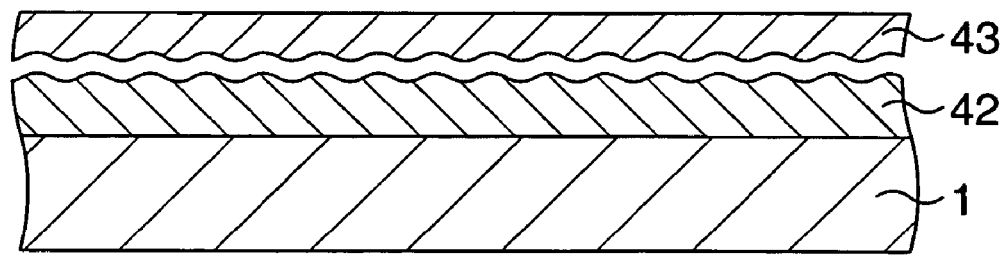
FIG. 23A and FIG. 23B are rough cross-sectional views showing, in the order of steps, a manufacturing method of a reference substrate for defect detection sensitivity calibration according to a modification example 1 of the second embodiment.
Figure 23B:
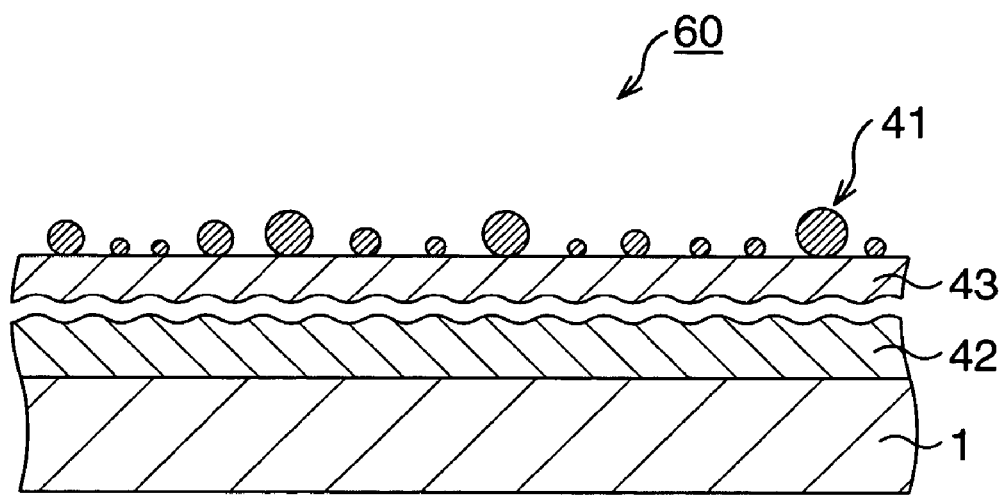

FIGS. 23A, 23B are rough cross-sectional views showing, in the order of steps, a manufacturing method of a reference substrate for defect detection sensitivity calibration according to the modification example 1 of the second embodiment.

First, as shown in FIG. 23A, a silicon oxide film is deposited by, for example, a CVD method via an interlayer insulation film 42 and so on, above a surface of a semiconductor substrate, for example, a silicon substrate 1, especially on portions where many target defect occurrences are observed, whereby an insulation film 43 is formed.

Subsequently, as shown in FIG. 23B, by the same method as that used in the second embodiment, particulates with nonuniform size are scattered on a surface of the insulation film 43. These particulates function as programmed defective portions 41. Here, parts where many target defect occurrences are observed are especially selected as areas for scattering the particulates. This enables efficient sensitivity calibration.

The silicon substrate 1 in which on the surface of the insulation film 43, the programmed defective portions 41 are thus formed by the scattering of the particulates with nonuniform size is used as a reference substrate 60 for defect detection sensitivity calibration of the modification example 1.

Incidentally, this example shows an example where programmed defective portions 37a to 37c are formed on the insulation film 43 formed above the silicon substrate 1, but for example, the programmed defective portions may be formed on a polycrystalline silicon film formed above the silicon substrate 1.

According to the modification example 1, the use of the reference substrate 60 for defect detection sensitivity calibration with an extremely simple structure makes it possible to fully ensure the defect detection sensitivity high enough to detect minute defects occurring in actual semiconductor processes and comparable to or higher than the defect detection sensitivity of the first embodiment, in particular, it is possible to provide an index, usable in manufacturing management, for determining sensitivity adjustment after the lamp 21a is replaced in the illumination part 21 of the defect detection apparatus.

MODIFICATION EXAMPLE 2

In this example, as a defect formation portion being a portion where programmed defective portions are formed, at least two portions are selected from a silicon substrate and at least one upper film formed above the silicon substrate.

FIGS. 24A to 24D are rough cross-sectional views showing, in the order of steps, a manufacturing method of a reference substrate for defect detection sensitivity according to the modification example 2 of the second embodiment.

Figure 24A:
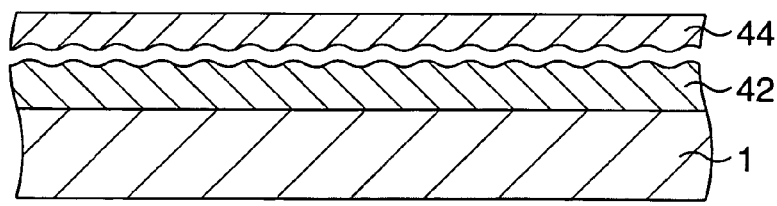
FIGS. 24A to FIG. 24D are rough cross-sectional views showing, in the order of steps, a manufacturing method of a reference substrate for defect detection sensitivity calibration according to a modification example 2 of the second embodiment.

First, as shown in FIG. 24A, a silicon oxide film made of a material transparent to illumination light of the lamp 21a in the illumination part 21 is deposited by, for example, a CVD method via an interlayer insulation film 42 and so on, above a surface of a semiconductor substrate, for example, a silicon substrate 1, in particular on portions where many target defect occurrences are observed, whereby an insulation film 44 is formed.

Figure 24B:
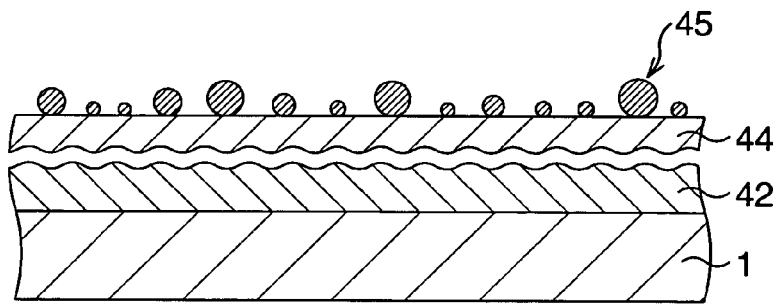

Subsequently, as shown in FIG. 24B, by the same method as that used in the second embodiment, particulates with nonuniform size are scattered on a surface of the insulation film 44. These particulates function as programmed defective portions 45. Here, parts where many target defect occurrences are observed are especially selected as areas for scattering the particulates. This enables efficient sensitivity calibration.

Figure 24C:
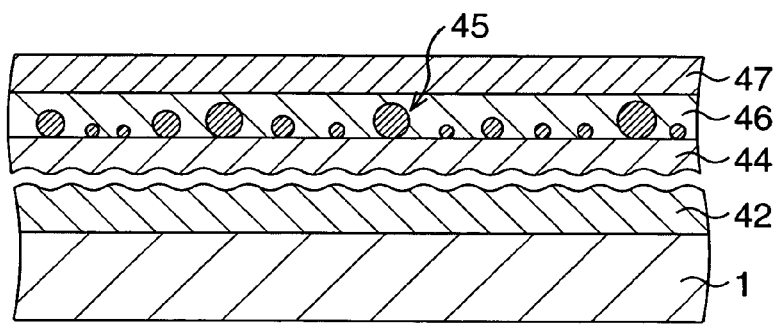

Subsequently, as shown in FIG. 24C, a silicon oxide film similarly made of a material transparent to the illumination light of the lamp 21a in the illumination part 21 is deposited on the insulation film 44 by, for example, a CVD method so as to cover the programmed defective portions 45, whereby an insulation film 46 is formed. Next, a silicon oxide film similarly made of a material transparent to the illumination light of the lamp 21a in the illumination part 21 is deposited on the insulation film 46 by, for example, a CVD method, whereby an insulation film 47 is formed. Here, the insulation film 47 is adjusted in film thickness as will be described later.

Figure 24D:
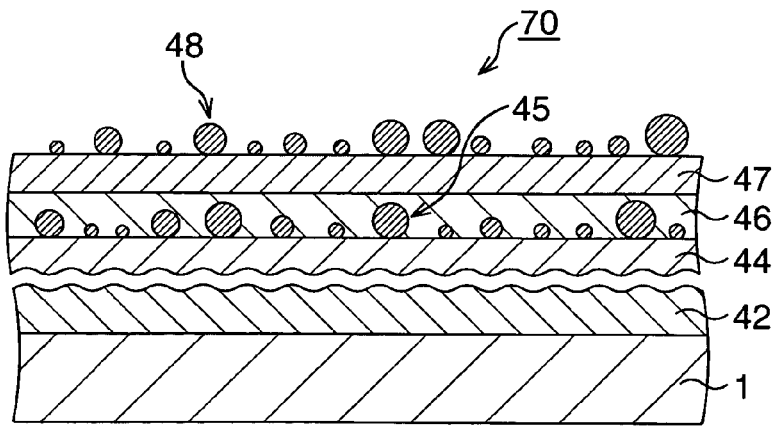

Subsequently, as shown in FIG. 24D, by the same method as that used in the second embodiment, particulates with nonuniform size are scattered on a surface of the insulation film 47. These particulates function as programmed defective portions 48. Here, parts where many target defect occurrences are observed are especially selected as areas for scattering the particulates. This enables efficient sensitivity calibration.

The silicon substrate 1 in which on the surfaces of the insulation films 44, 47, the programmed defective portions 45, 48 are thus formed by the scattering of the particulates with nonuniform size is used as a reference substrate 70 for defect detection sensitivity calibration of this modification example 2.

In this example, the thickness of the insulation film 47 (and an upper portion of the insulation film 46) is adjusted so as to satisfy conditions under which two kinds of illumination lights are strengthened by each other or are cancelled out by each other based on difference in optical path difference, the two kinds of illumination lights being reflected (scattered) light which is the illumination light emitted from the lamp 21a in the illumination part 21 and reflected (scattered) on the programmed defective portions 48, and reflected (scattered) light which is the illumination light reflected (scattered) on the programmed defective portions 45 after passing through the insulation film 47 (and the upper portion of the insulation film 46). This enables accurate and sure calibration of focus change.

According to the modification example 2, the use of the reference substrate 70 for defect detection sensitivity calibration with an extremely simple structure makes it possible to fully ensure defect detection sensitivity high enough to detect minute defects occurring in actual semiconductor processes and comparable to or higher than the defect detection sensitivity of the first embodiment and, in particular, it is possible to provide an index, usable in manufacturing management, for determining sensitivity adjustment after the lamp 21a is replaced in the illumination part 21 of the defect detection apparatus.

The present invention is capable of sufficiently ensuring defect detection sensitivity high enough to detect microscopic defects occurring in actual semiconductor processes and in particular, is capable of providing an index, usable in manufacturing management, for determining sensitivity adjustment after a light source of an illumination part of a defect inspection apparatus is replaced.

The present embodiments are to be considered in all respects as illustrative and no restrictive, and all changes which come within the meaning and range of equivalency of the claims are therefore intended to be embraced therein. The invention may be embodied in other specific forms without departing from the spirit or essential characteristics thereof.

What is claimed is:

1. A substrate for defect detection sensitivity calibration, used for calibrating detection sensitivity of a defect detection apparatus detecting a defective portion occurring in a device, used for detecting defection with the defect detection apparatus, the substrate comprising:
    a defect formation portion; and
    a plurality of programmed defective portions formed on a surface of said defect formation portion,
    wherein said programmed defective portions are formed to have arbitrary sizes,
    a pattern portion provided on the surface of said defect formation portion and having a predetermined pattern, wherein said programmed defective portions that form dents by protruding outwards are located on denting portions between side by side pattern portions;
    wherein particles are part of a material of the pattern that adheres on a surface of the defect formation portion when the pattern is formed by processing; and
    wherein each of said programmed defective portions is a protruding structure that is formed by processing the surface of said defect formation portion, with an arbitrary plural number of the particles adhering on the surface of said defect formation portion functioning as a mask, and is formed by integrating the defect formation portion with same material of the defect formation portion.

2. The substrate for defect detection sensitivity calibration according to claim 1, wherein said programmed defective portions have heights whose values are equal to or smaller than ten times a value of a dimension of the pattern.

3. The substrate for defect detection sensitivity calibration according to claim 1, wherein said programmed defective portions are in a conical shape.

4. The substrate for defect detection sensitivity calibration according to claim 1, wherein said defect formation portion is a substrate.

5. The substrate for defect detection sensitivity calibration according to claim 1, wherein said defect formation portion is a thin film formed above a substrate.

6. The substrate for defect detection sensitivity calibration according to claim 1, wherein said defect formation portion is comprised of at least two layers having said particulates thereon; and
wherein said layers are selected from the group consisting of an underlying substrate and a thin film formed above the underlying substrate.

7. A manufacturing method of a substrate for defect detection sensitivity calibration, used for calibrating detection sensitivity of a defect detection apparatus detecting a defective portion formed in a device, used for detecting defection with the defect detection apparatus, the method comprising:
depositing a material film for forming a predetermined pattern on a surface of a defect formation portion;
forming a pattern portion having the pattern by processing the material film;
forming programmed defective portions with arbitrary sizes by processing the surface of the defect formation portion, with an arbitrary plural number of particles, which are part of the material film adhering on the surface of the defect formation portion, functioning as a mask; and wherein said programmed defective particles that form dents by protruding outwards are located on denting portions between side by side pattern portions;
wherein each of said programmed defective portions is a protruding structure that is formed by integrating the defect formation portion with same material of the defect formation portion.

8. The manufacturing method of the substrate for defect detection sensitivity calibration according to claim 7, further comprising, after said forming the programmed defective portions, removing the pattern made of the material film.

9. The manufacturing method of the substrate for defect detection sensitivity calibration according to claim 7, wherein said defect formation portion is a substrate.

10. The manufacturing method of the substrate for defect detection sensitivity calibration according to claim 7, wherein said defect formation portion is a thin film formed above a substrate.

11. A sensitivity calibration method for a defect inspection apparatus which performs defect inspection by using a substrate for defect detection sensitivity calibration and by irradiating the substrate for defect detection sensitivity calibration with light from an illumination part to detect the light reflected on the substrate for defect detection sensitivity calibration,
wherein the substrate for defect detection sensitivity calibration comprises:
a defect formation portion; and
a plurality of programmed defective portions with arbitrary sizes formed on a surface of the defect formation portion, and the method comprising:
detecting the programmed defective portions in the substrate for defect detection sensitivity calibration before the light source is replaced;
replacing the light source;
detecting the programmed defective portions in the substrate for defect detection sensitivity calibration after the light source is replaced; and
calculating a difference between the number of the programmed defective portions detected before the replacement of the light source and the number of the programmed defective portions detected after the replacement of the light source, and based on the calculated value, correcting the focus change of the defect detection apparatus for making the number of the programmed defective portions detected after the replacement of the light source equal to the number of the programmed defective portions detected before the replacement of the light source.

12. The sensitivity calibration method for the defect inspection apparatus according to claim 11, wherein each of the programmed defective portions is a protruding structure that is formed by processing the surface of the defect formation portion, with an arbitrary plural number of particles adhering on the surface of the defect formation portion functioning as a mask.

13. The sensitivity calibration method for the defect inspection apparatus according to claim 11,
wherein the substrate for defect detection sensitivity calibration further comprises a pattern portion provided on the surface of the defect formation portion and having a predetermined pattern, and
wherein the particles are part of a material of the pattern that adheres on the surface of the defect formation portion when the pattern is formed by processing.

14. The sensitivity calibration method for the defect inspection apparatus according to claim 11, wherein said programmed defective portions are particulates with arbitrary sizes scattered on the surface of the defect formation portion.

15. The sensitivity calibration method for the defect inspection apparatus according to claim 11, wherein the defect formation portion is a substrate.

16. The sensitivity calibration method for the defect inspection apparatus according to claim 11, wherein the defect formation portion is a thin film formed above a substrate.

17. The sensitivity calibration method for the defect inspection apparatus according to claim 14, wherein said defect formation portion is comprised of at least two layers having said particulates thereon; and
wherein said layers are selected from the group consisting of an underlying substrate and a thin film formed above the underlying substrate.

18. A defect inspection apparatus comprising:
a substrate for defect detection sensitivity calibration that includes a defect formation portion and a plurality of programmed defective portions with arbitrary sizes formed on a surface of the defect formation portion and a pattern portion provided on the surface of said defect formation portion and having a predetermined pattern, wherein said programmed defective portions that form dents by protruding outwards are located on denting portions between side by side pattern portions, wherein particles are part of a material of the pattern that adheres on a surface of the defect formation portion when the pattern is formed by processing and wherein each of said programmed defective portions is a protruding structure that is formed by processing the surface of said defect formation portion, with an arbitrary plural number of the particles adhering on the surface of said defect formation portion functioning as a mask, and is formed by integrating the defect formation portion with same material of the defect formation portion;

an illumination part having a light source and irradiating said substrate for defect detection sensitivity calibration with light;
a detecting unit detecting the light reflected on said substrate for defect detection sensitivity calibration;
a counting unit counting the number of the programmed defective portions, which are detected by said detecting unit, of said substrate for defect detection sensitivity calibration; and
a calculating unit which calculates a difference between the number of the programmed defective portions detected before the light source is replaced and the number of the programmed defective portions detected after the light source is replaced.

19. The defect inspection apparatus according to claim 18, wherein the defect formation portion is a substrate.

20. The defect inspection apparatus according to claim 18, wherein the defect formation portion is a thin film formed above a substrate.

21. The defect inspection apparatus according to claim 18, wherein said defect formation portion is comprised of at least two portions layers having said particulates thereon; and
wherein said layers are selected from the group consisting of an underlying substrate and a thin film formed above the underlying substrate.

* * * * *